(12) United States Patent
Willard et al.

(10) Patent No.: US 6,309,379 B1
(45) Date of Patent: Oct. 30, 2001

(54) SHEATH FOR SELECTIVE DELIVERY OF MULTIPLE INTRAVASCULAR DEVICES AND METHODS OF USE THEREOF

(76) Inventors: Lloyd K. Willard, Rte. 2 Box 5-B, Miltona, MN (US) 56354; Mark Whalen, 2001 Ridgewwod, Alexandria, MN (US) 56308; Wayne Sieben, 3707 Nakomis, Alexandria, MN (US) 56308

( * ) Notice: Subject to any disclaimer, the term of this patent is extended or adjusted under 35 U.S.C. 154(b) by 0 days.

(21) Appl. No.: 08/035,379

(22) Filed: Mar. 22, 1993

Related U.S. Application Data

(63) Continuation-in-part of application No. 07/946,000, filed on Sep. 15, 1992, now abandoned, which is a continuation of application No. 07/704,828, filed on May 23, 1991, now abandoned, which is a continuation-in-part of application No. 07/809,715, filed on Dec. 18, 1991, now Pat. No. 5,219,335.

(51) Int. Cl.$^7$ ..................................................... A61B 8/14
(52) U.S. Cl. ................... 604/467; 604/102.02; 604/500; 604/523
(58) Field of Search ................................... 604/43, 96.01, 604/101.01–103.14, 164.01, 164.05, 164.09, 164.13; 600/462–463, 467

(56) References Cited

U.S. PATENT DOCUMENTS

| | | |
|---|---|---|
| 3,670,729 | * 6/1972 | Bennett et al. . |
| 3,769,981 | 11/1973 | McWhorter . |
| 3,915,168 | 10/1975 | Monestere, Jr. et al. . |
| 4,033,331 | 7/1977 | Guss et al. . |
| 4,052,989 | 10/1977 | Kline . |
| 4,149,535 | * 4/1979 | Volder . |
| 4,270,535 | 6/1981 | Bogue et al. . |
| 4,367,740 | 1/1983 | Evanoski, III . |
| 4,540,402 | 9/1985 | Aigner . |
| 4,552,554 | 11/1985 | Gould et al. . |

(List continued on next page.)

FOREIGN PATENT DOCUMENTS

| | | |
|---|---|---|
| 26 44 020 | 4/1978 | (DE) . |
| 29 29 562 | 1/1980 | (DE) . |
| 0 093 887 | 11/1983 | (EP) . |
| 0 132 215 | 1/1985 | (EP) . |
| 0 380 102 | 8/1990 | (EP) . |
| PCT/WO/92 11055 | 7/1992 | (WO) . |

*Primary Examiner*—Mark Bockelman
(74) *Attorney, Agent, or Firm*—Lyon & Lyon LLP

(57) ABSTRACT

An intravascular device, such as a sheath, and methods for use thereof for selective alternate positioning of other intravascular devices having predetermined sizes in a distal vascular region of the body of a patient. The intravascular selection sheath comprises a tubular body having proximal, intermediate and distal sections and a lumen extending therethrough. The portion of the lumen in the distal section can be occupied by only one of the other intravascular devices of the predetermined sizes at a given time. The portion of the selection sheath lumen in the intermediate section can be occupied by at least two intravascular devices of the predetermined sizes in a side by side relationship. In operation, the two other intravascular devices occupy positions in the lumen in the intermediate section of the selection sheath. First, one of the intravascular devices can be advanced into the lumen in the distal section of the selection sheath and then withdrawn back into the intermediate section. Next, the other of the intravascular devices can be advanced from the intermediate section into the distal section of the selection sheath, thereby allowing for multiple diagnostics, therapies, or other procedures to be performed alternatively. The other intravascular devices that occupy positions in the sheath lumen can be exchanged for yet further intravascular devices. This selection sheath geometry can also be incorporated in intravascular devices that provide therapeutic and/or diagnostic functions.

17 Claims, 20 Drawing Sheets

U.S. PATENT DOCUMENTS

| | | |
|---|---|---|
| 4,577,637 | 3/1986 | Mueller, Jr. . |
| 4,601,701 | 7/1986 | Mueller, Jr. . |
| 4,619,643 | 10/1986 | Bai . |
| 4,661,110 | 4/1987 | Fortier et al. . |
| 4,730,616 * | 3/1988 | Frisbie et al. . |
| 4,748,982 | 6/1988 | Horzewski et al. . |
| 4,769,005 | 9/1988 | Ginsburg et al. . |
| 4,772,268 | 9/1988 | Bates . |
| 4,787,892 | 11/1988 | Rosenberg . |
| 4,798,193 | 1/1989 | Giesy et al. . |
| 4,820,349 * | 4/1989 | Saab . |
| 4,824,435 | 4/1989 | Giesy et al. . |
| 4,834,102 | 5/1989 | Schwarzchild et al. . |
| 4,842,582 | 6/1989 | Mahurkar . |
| 4,922,924 | 5/1990 | Gambale . |
| 4,928,693 | 5/1990 | Goodin et al. . |
| 4,932,413 | 6/1990 | Shockey et al. . |
| 4,955,863 | 9/1990 | Walker et al. . |
| 4,957,484 | 9/1990 | Murtfeldt . |
| 4,961,809 | 10/1990 | Martin . |
| 4,976,689 | 12/1990 | Buchbinder et al. . |
| 4,998,916 | 3/1991 | Hammerslag et al. . |
| 4,998,919 | 3/1991 | Schnepp-Pesch et al. . |
| 5,009,636 | 4/1991 | Wortley et al. . |
| 5,024,234 | 6/1991 | Leary et al. . |
| 5,029,580 | 7/1991 | Radford et al. . |
| 5,053,023 | 10/1991 | Martin . |
| 5,054,492 | 10/1991 | Scribner et al. . |
| 5,057,073 | 10/1991 | Martin . |
| 5,059,177 | 10/1991 | Towne et al. . |
| 5,203,338 * | 4/1993 | Tang ................................ 128/662.06 |
| 5,217,482 * | 6/1993 | Keith . |
| 5,219,335 * | 6/1993 | Willard et al. ........................ 604/164 |
| 5,295,961 * | 3/1994 | Niederhauser et al. . |
| 5,304,134 * | 4/1994 | Kraus et al. . |
| 5,370,655 * | 12/1994 | Burns . |
| 5,649,909 * | 7/1997 | Cornelius . |

* cited by examiner

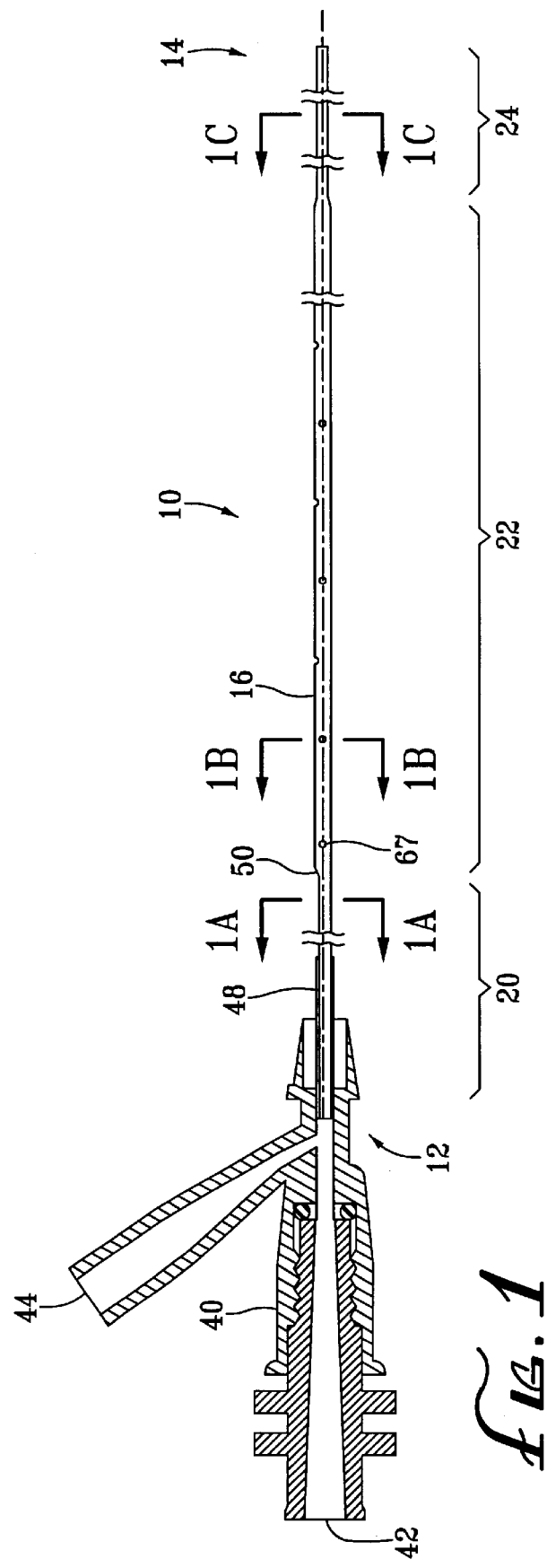

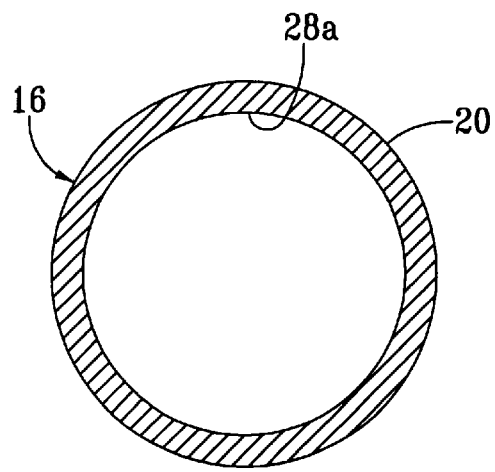
_fig. 1A_
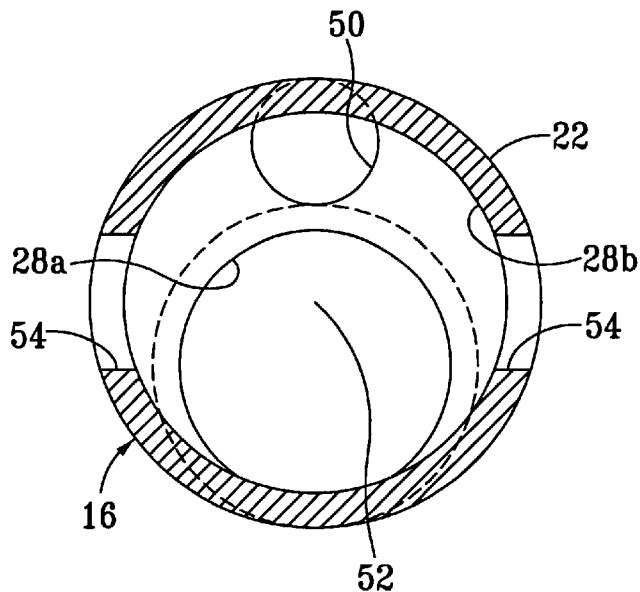
_fig. 1B_
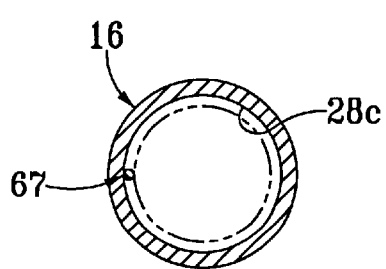
_fig. 1C_

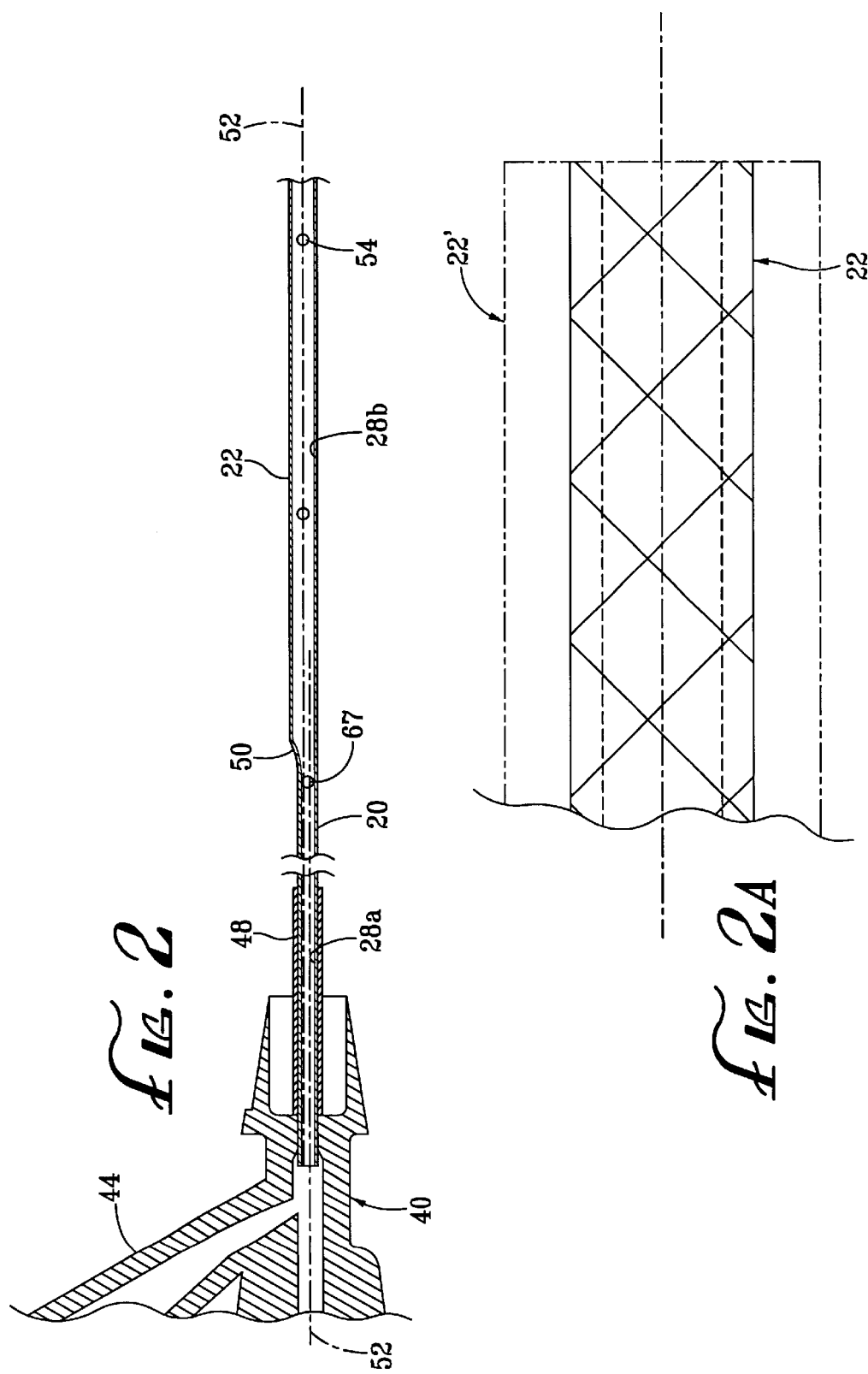

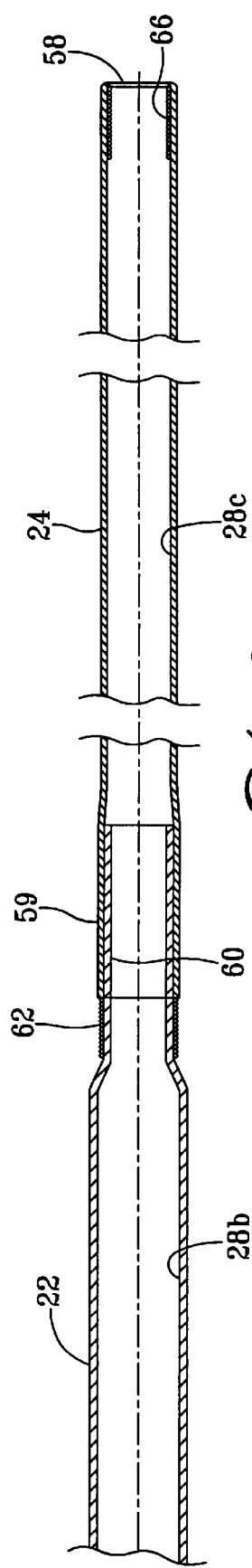
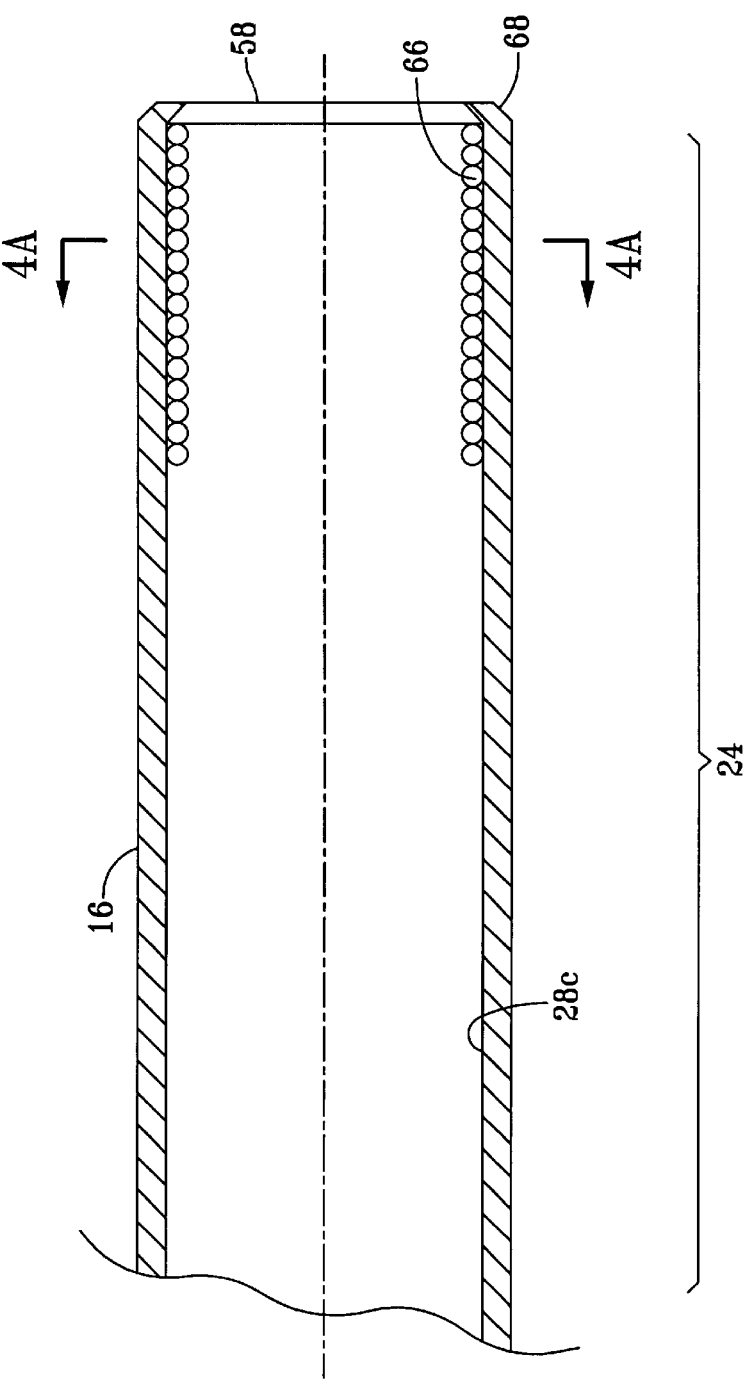
Fig. 3
Fig. 4

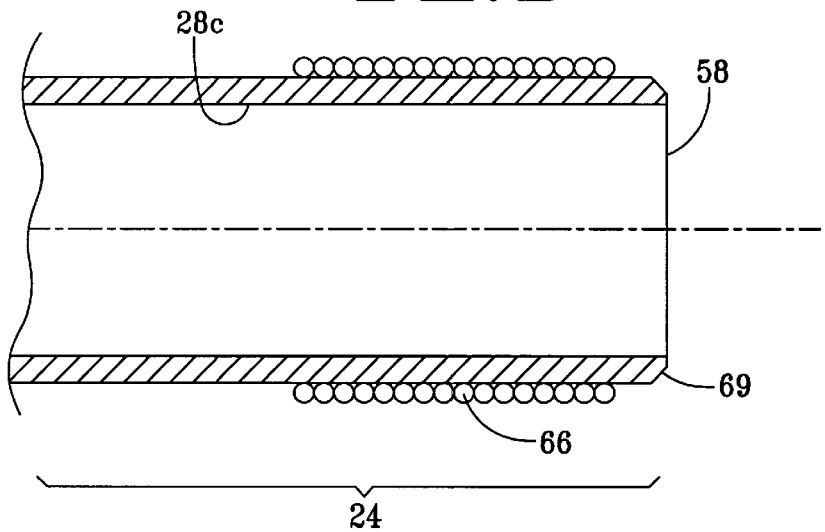
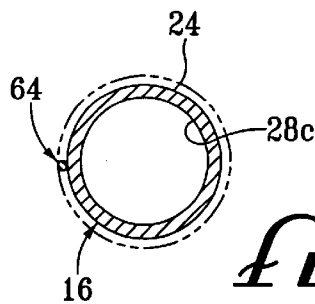
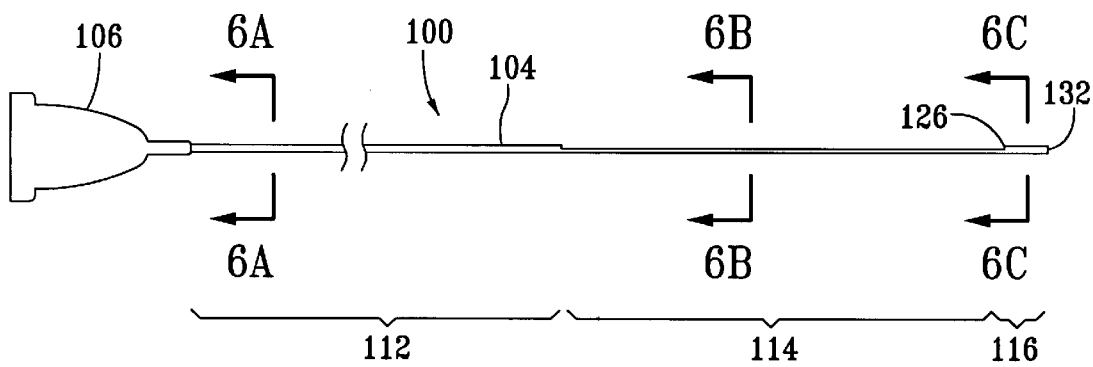

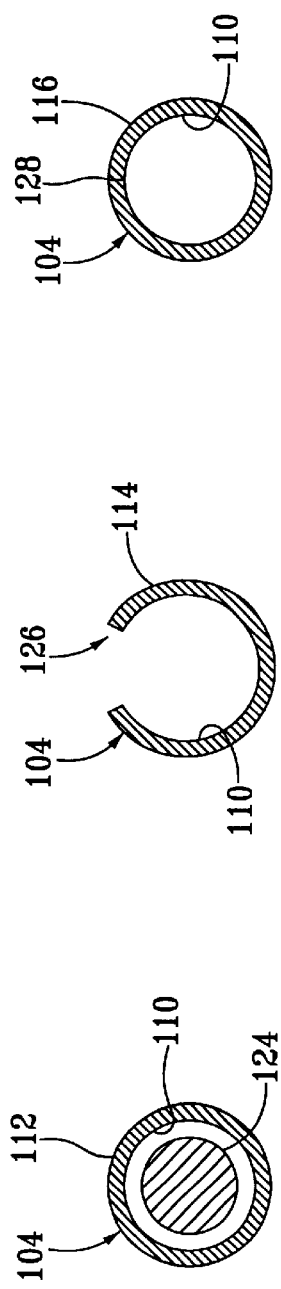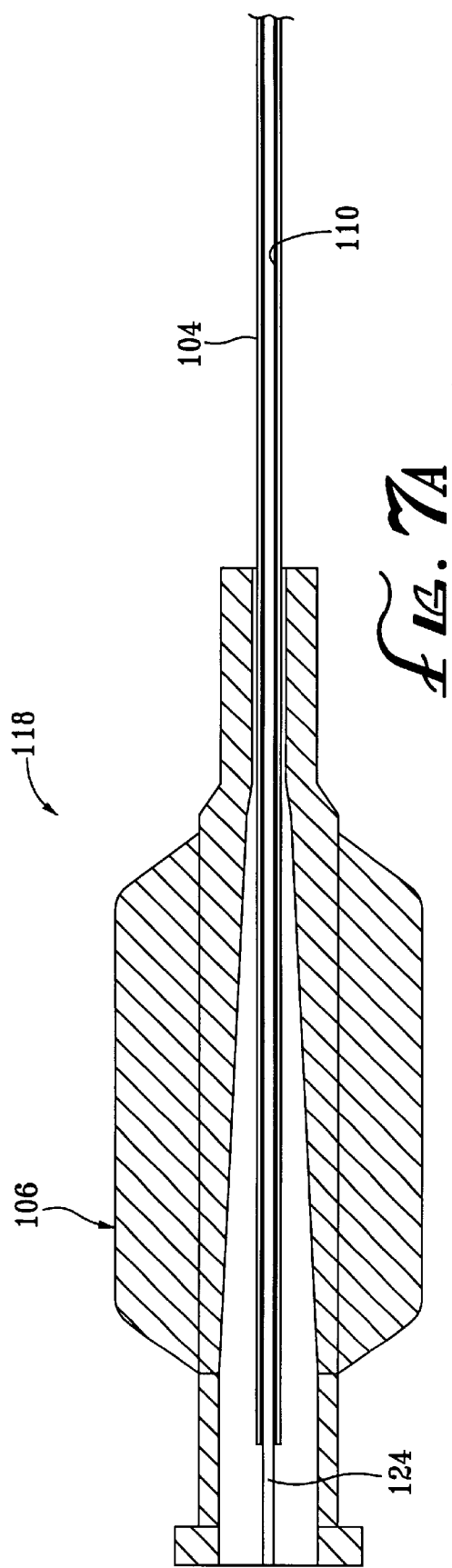

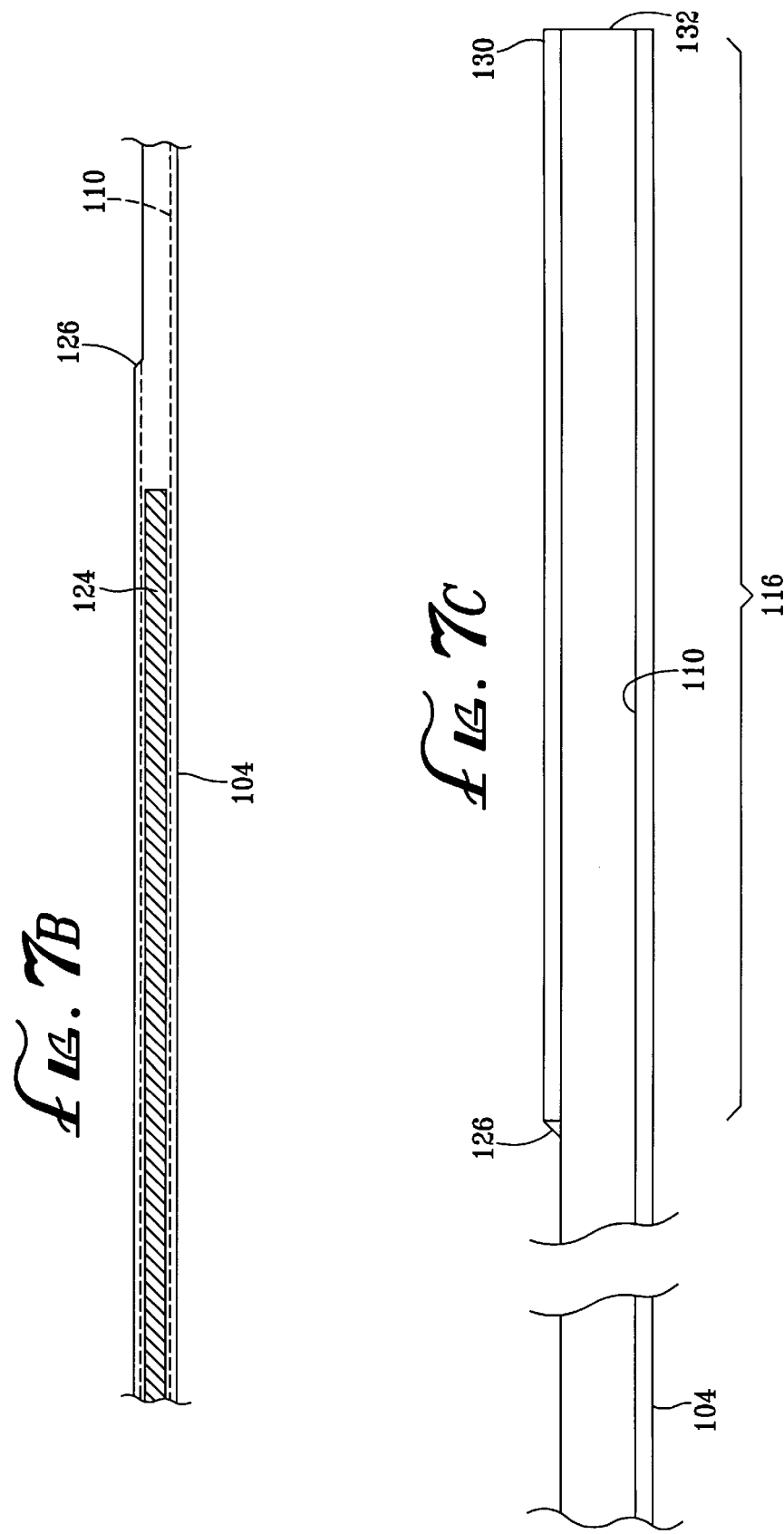

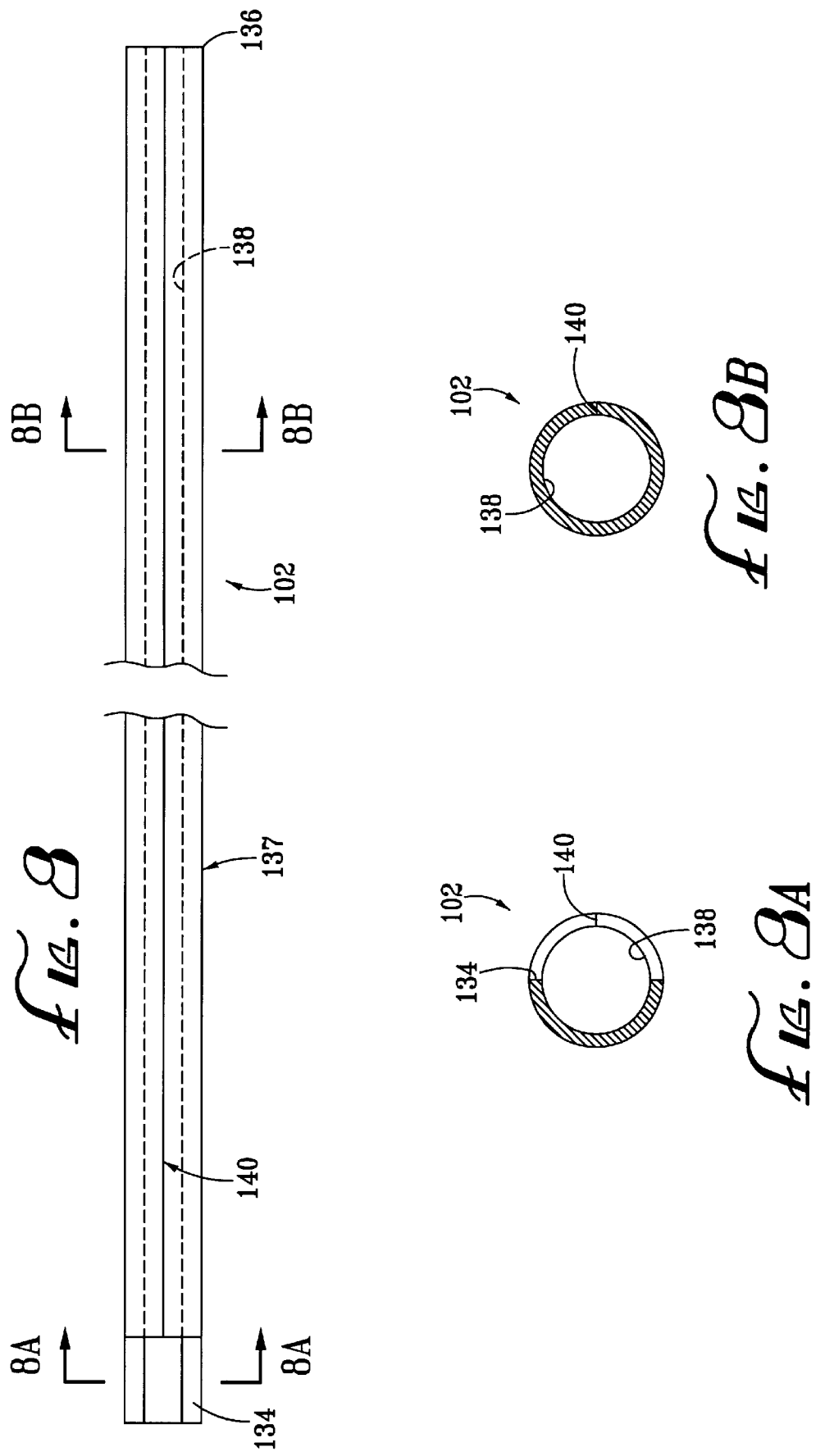

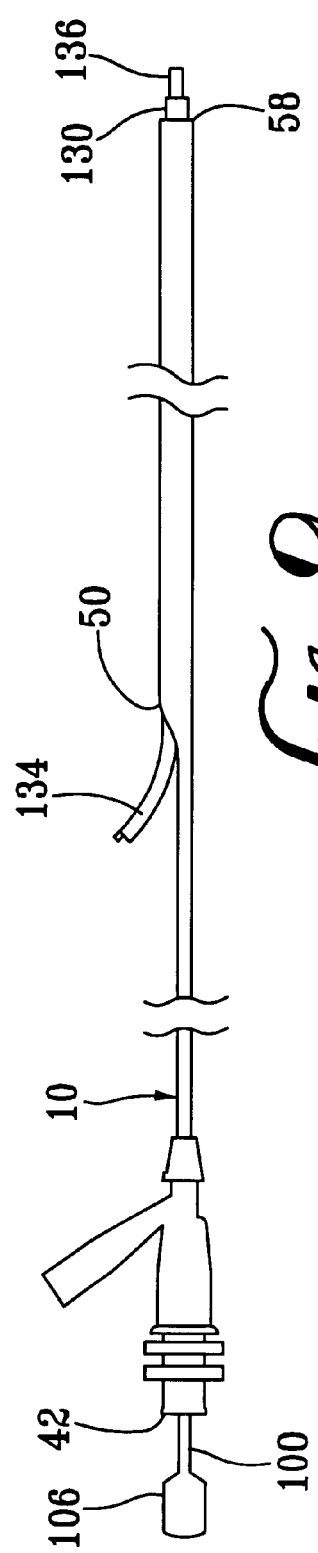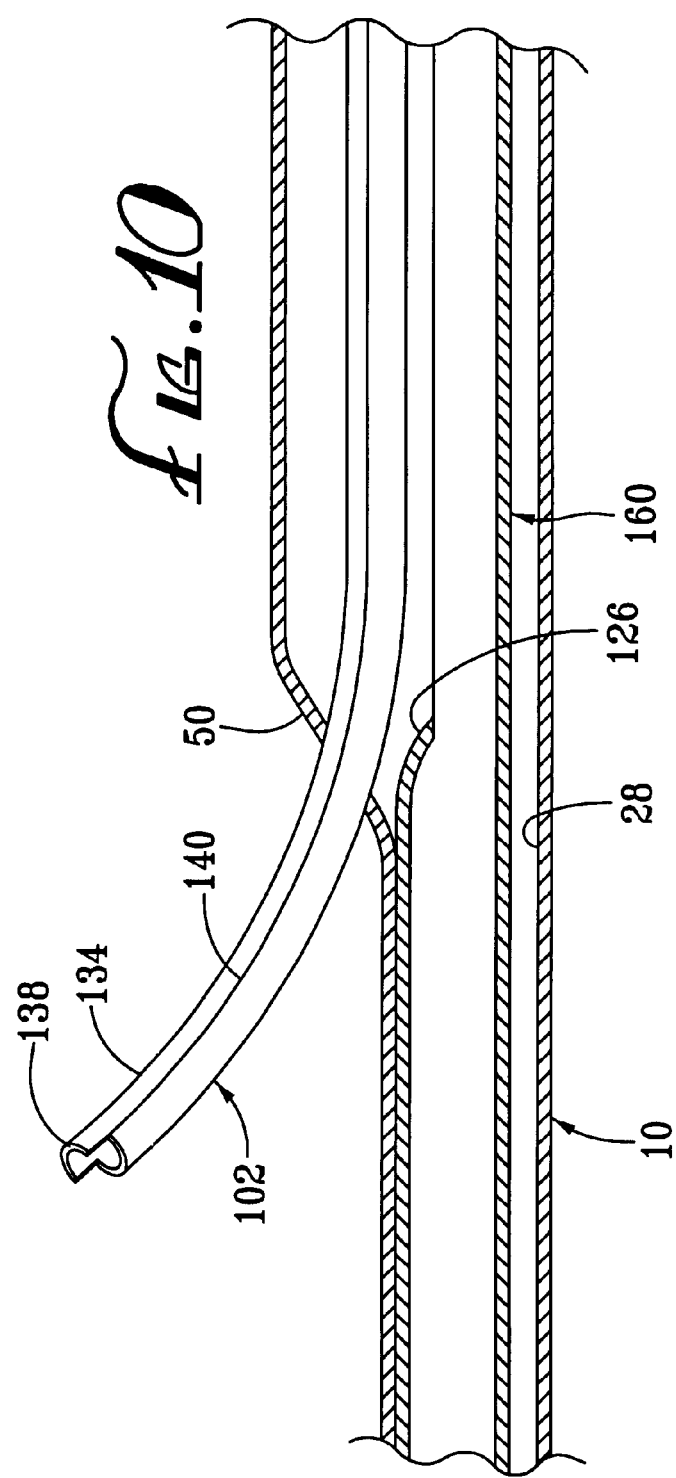

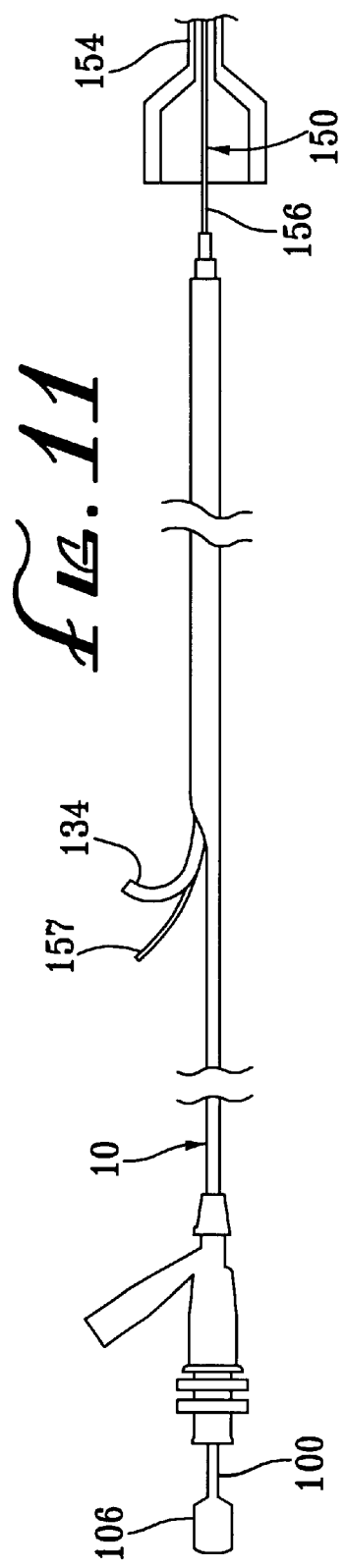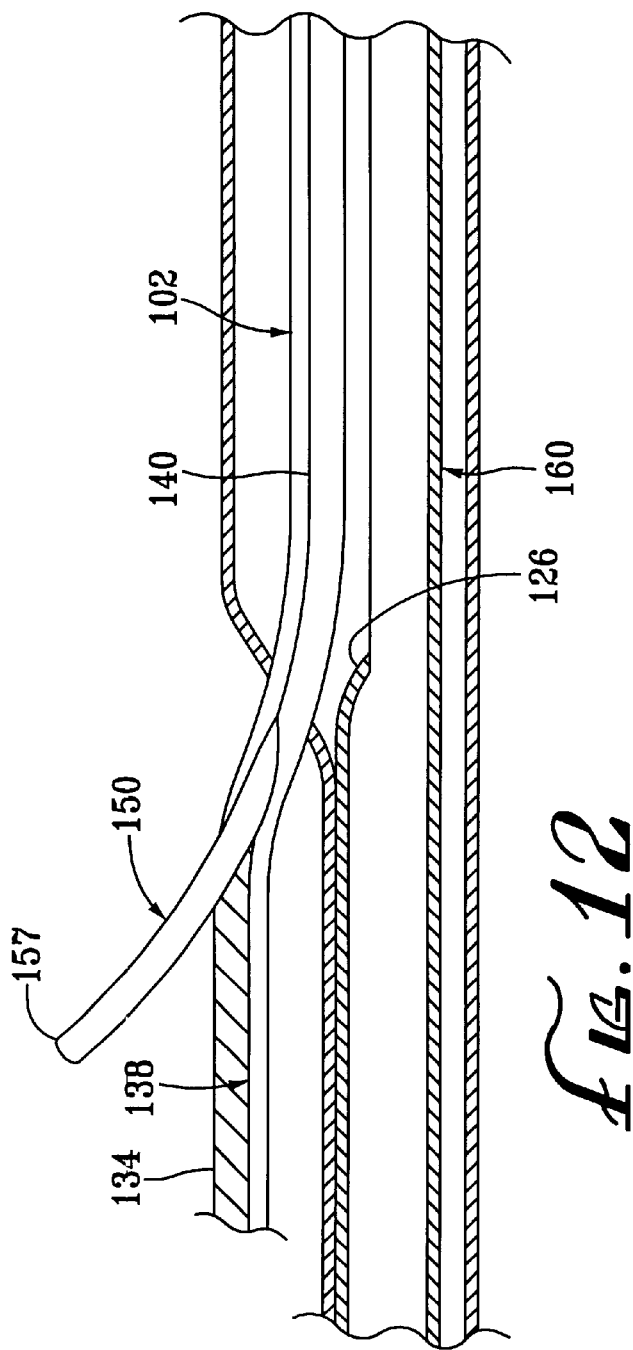
Fig. 11
Fig. 12

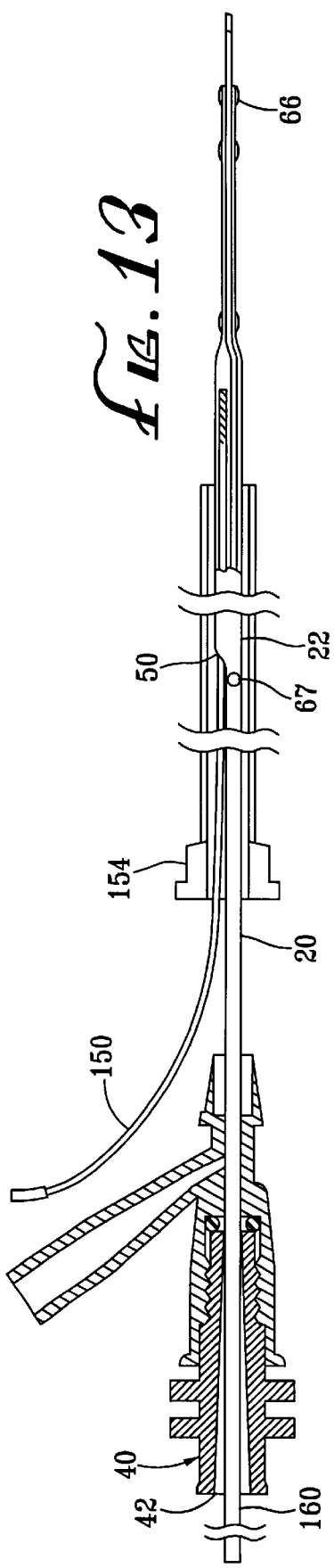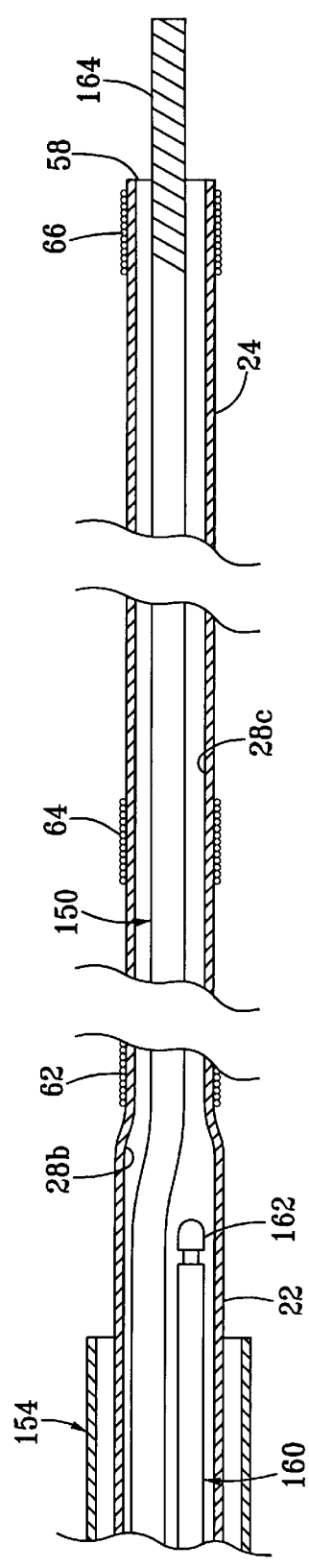

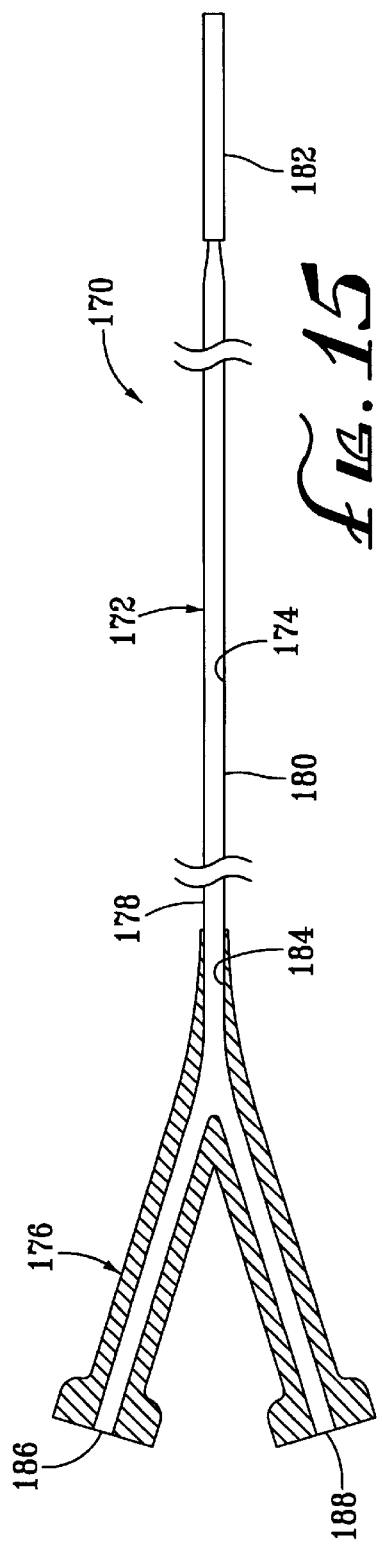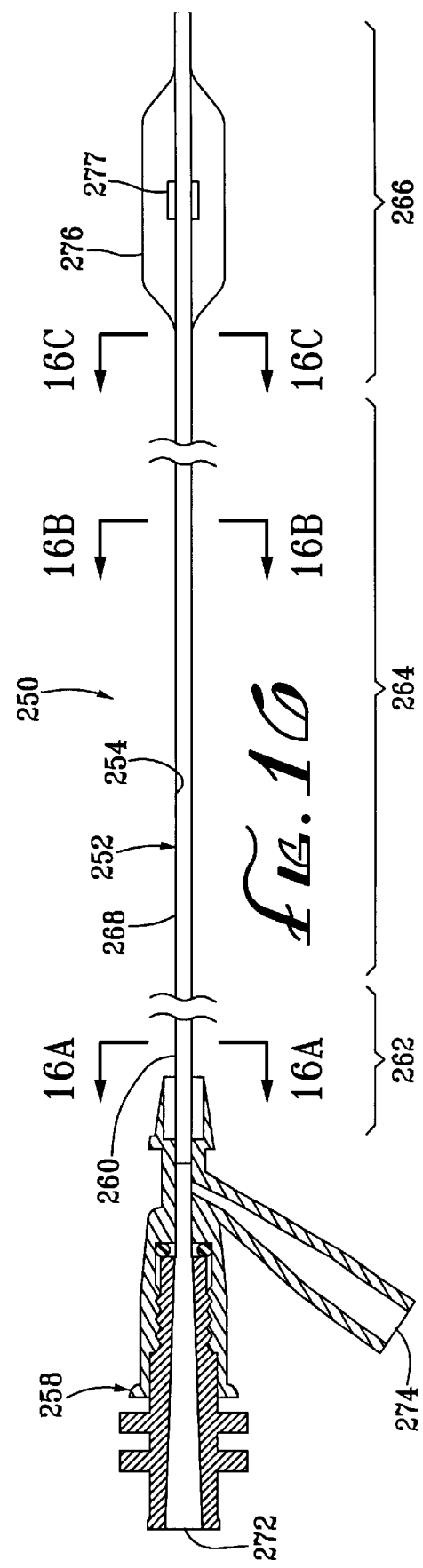

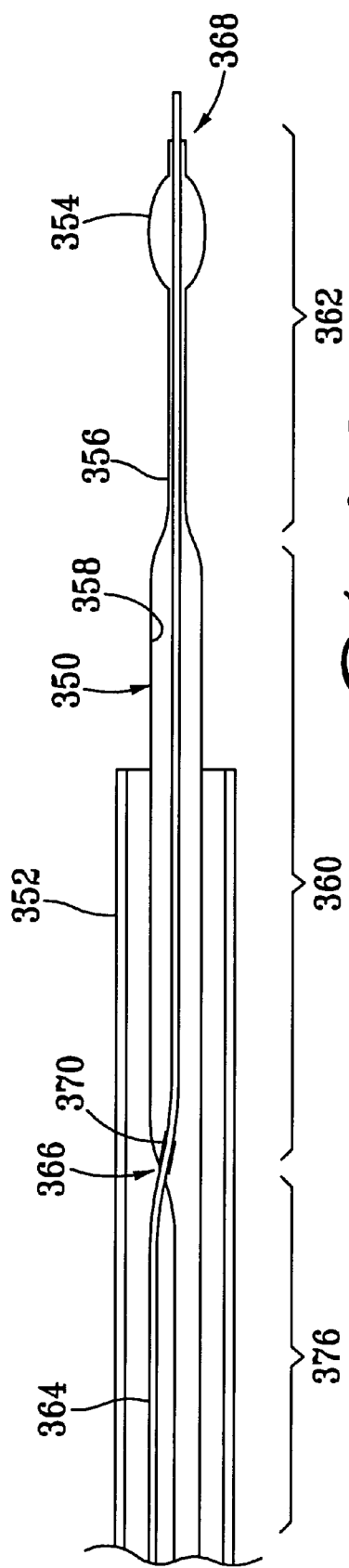
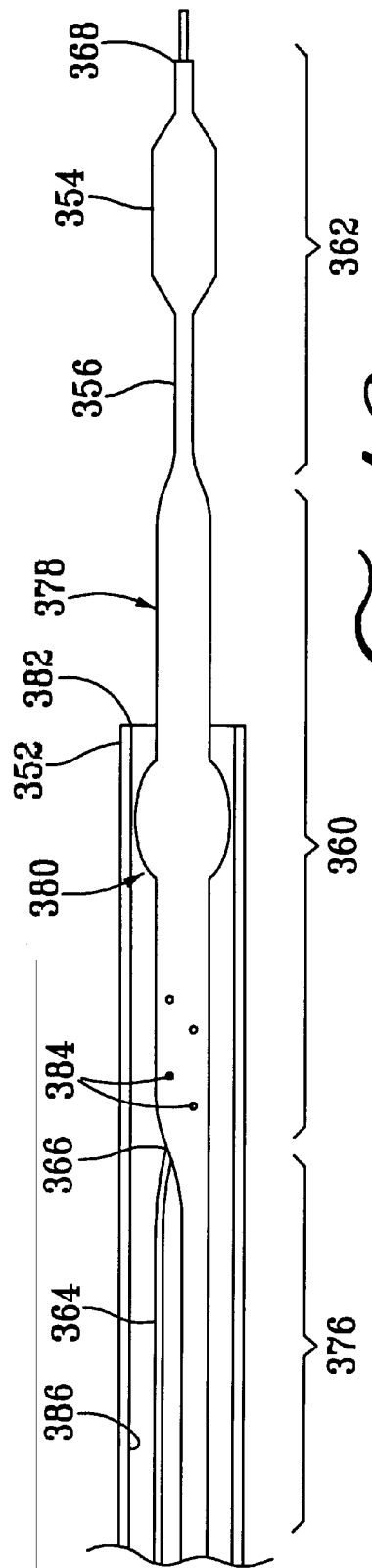
Fig. 17
Fig. 18

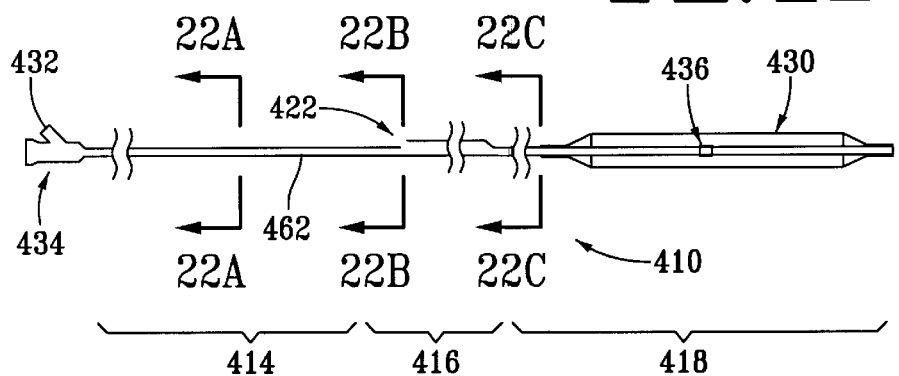
FIG. 22
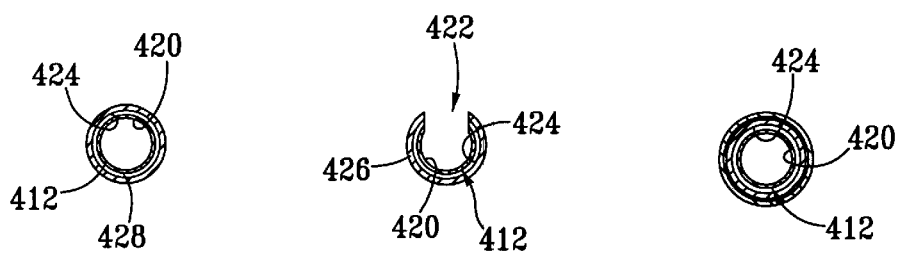
FIG. 22A  FIG. 22B  FIG. 22C
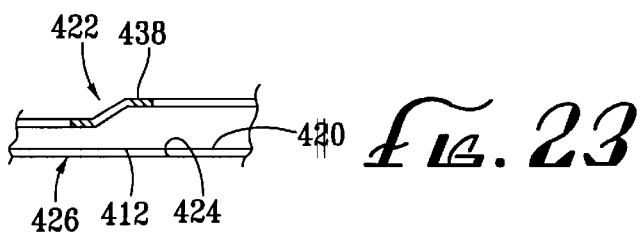
FIG. 23
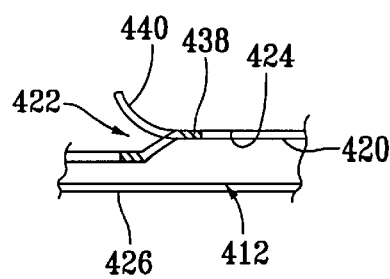 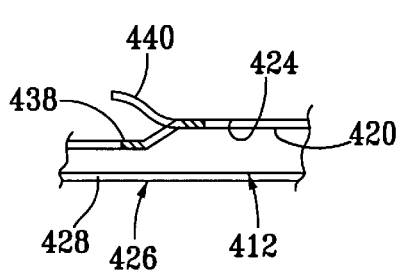
FIG. 24A  FIG. 24B

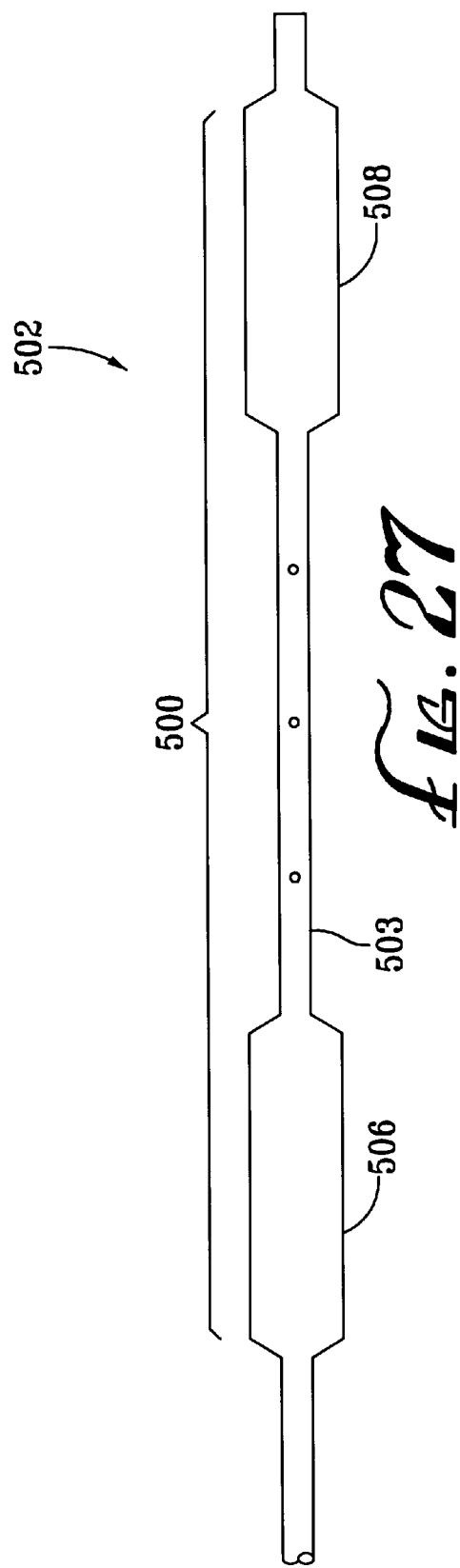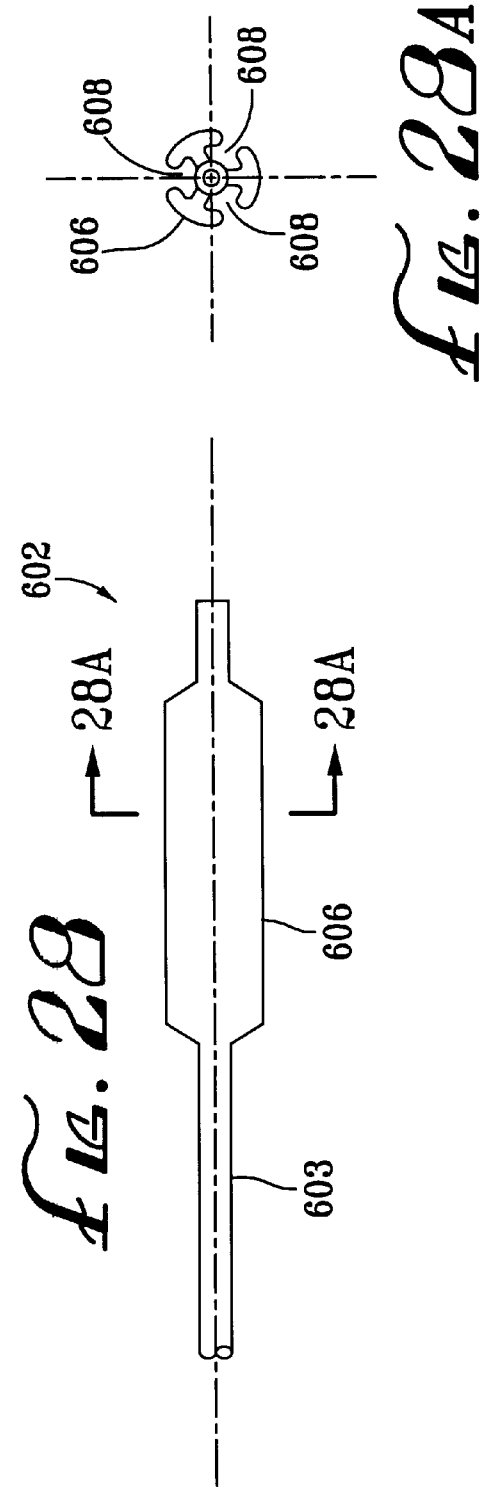

SHEATH FOR SELECTIVE DELIVERY OF MULTIPLE INTRAVASCULAR DEVICES AND METHODS OF USE THEREOF

REFERENCE TO RELATED APPLICATIONS

This application is a continuation-in-part of:
(1) Ser. No. 07/946,000, filed Sep. 15, 1992 now abandoned which is a continuation of Ser. No. 07/704,828 filed May 23, 1991 now abandoned; and
(2) Ser. No. 07/809,715 filed Dec. 18, 1991, U.S. Pat. No. 5,219,335 all the disclosures of which are incorporated herein by reference in their entirety.

FIELD OF THE INVENTION

The present invention relates to a new class of intravascular devices and in particular to an intravascular device such as a selective delivery sheath used for positioning multiple other intravascular devices such as catheters, ultrasonic imagers, guide wires, or other devices in the vascular system of a patient. The present invention also relates to an intravascular device such as a balloon catheter that incorporates the new selective delivery sheath construction technology or methods.

BACKGROUND OF THE INVENTION

In the above referred-to applications, a new type of intravascular devices was disclosed. The new type of intravascular devices provided for the selective positioning of multiple other intravascular devices into a distal vascular region.

Interventional cardiology and interventional radiology have developed rapidly in recent years. Interventional therapies such as balloon angioplasty and atherectomy are now regularly employed in the treatment of vascular disease or other conditions that occlude or reduce the lumen size of portions of the vascular system. Additional therapeutic technologies and treatments hold promise for providing further advancement against vascular diseases.

In addition, intravascular diagnostic techniques have been developed to measure or image the extent of an occlusion of a vessel, (e.g. stenosis). Such diagnostic techniques include ultrasonic imaging, fiber optic imaging, Doppler and other flow measurements, and so on.

The above noted therapies and diagnostic techniques have achieved acceptance because of their effectiveness as well as the fact that they can be performed through a minor surgical procedure that is relatively non-disruptive to the patient. Therapeutic and diagnostic procedures, such as those described above, rely on the positioning of a device into the vascular system of a patient via an incision at a location, such as the femoral artery, that is remote from the site of the stenosis. Because the aforementioned therapies and diagnostic procedures rely upon positioning a device in the affected area, an important defining factor limiting the effective deployment of any of these devices is how small the device can be made. It is often in vessels of small inner diameters or tortuous passageways that stenosis occurs. Thus, it is often preferable to make such therapeutic and diagnostic devices as small as possible to fit into remote coronary sites or other vessel locations where the vessel lumen inner diameters are very small.

In order to facilitate placement and positioning of such therapeutic or diagnostic devices into distal vessel sites, positioning devices, such as guide wires and guide catheters, may be used. Guide wires are used to obtain a position in a distal vessel site so that other intravascular devices, such as a therapeutic or diagnostic device, can be advanced over the guide wire to the distal vessel site. Guide wires may be considered to support and facilitate the other types of interventional devices. Numerous kinds of guide wires are available, including steerable types. Guide wires may also be used therapeutically to open a passageway through a blocked vessel.

It is sometimes necessary to exchange one intravascular device for another. For example, it is sometimes necessary to exchange one balloon catheter for another of a different size or exchange a balloon catheter for another therapeutic or diagnostic device, if it is determined to be needed. Also, it is sometimes necessary to exchange guide wires, for example, if the physician is unable to cross a stenosis with the original guide wire. It is also sometimes necessary to use two balloons during the same procedure. Although presently available guide wires, guide catheters, and balloon dilation catheters provide for a degree of exchangeability, presently available intravascular devices are not readily exchangeable with newer emerging technologies or devices.

Accordingly, it is an object of the present invention to provide a new intravascular device that facilitates use and placement of multiple other intravascular devices in a vessel of a patient.

SUMMARY OF THE INVENTION

According to a first aspect of the invention, there are provided an intravascular device, such as a sheath, and methods for use thereof for selective positioning of multiple other intravascular devices in a distal vascular region of the body of a patient. The multiple other intravascular devices include, for example, a first intravascular device of a first predetermined size and a second intravascular device of a second predetermined size. The intravascular sheath comprises a tubular body having proximal, intermediate, and distal sections and a lumen extending therethrough. The portion of the lumen in the distal section is adapted and dimensioned to be occupied by a single vascular device of the predetermined sizes. The portion of the lumen in the intermediate section is dimensioned and adapted to be occupied by the two intravascular devices of the predetermined sizes in an adjacent, or side-by-side, relationship. In operation, two intravascular devices can occupy positions in the lumen in the intermediate section of the sheath at the same time. One of the intravascular devices is advanced into the lumen in the distal section of the sheath, or beyond, and a procedure may be performed. The first intravascular device is withdrawn back into the intermediate section, and then the other of the intravascular devices is advanced into or beyond the distal section. This allows for multiple diagnostics, therapies, or other procedures to be performed alternatively in a distal vascular region of the patient's body in which the distal section of the sheath is positioned.

In yet a further aspect of the present invention, the sheath construction can be incorporated into a therapeutic or diagnostic device such as a balloon catheter. This enables other therapies to be selected and employed in conjunction with a balloon dilation. The present invention offers the advantage of exchanging multiple devices by withdrawing one or the other into the intermediate region, thus saving time and reducing trauma to the vessel.

BRIEF DESCRIPTION OF THE DRAWINGS

FIG. 1 shows a longitudinal sectional view of a first embodiment of the present invention.

FIG. 1A is a cross section of the elongate tubular body of the embodiment of FIG. 1 taken along line A–A'.

FIG. 1B is a cross section of the elongate tubular body of the embodiment of FIG. 1 taken along line B–B'.

FIG. 1C is a cross section of the elongate tubular body of the embodiment of FIG. 1 taken along line C–C'.

FIG. 2 shows a longitudinal sectional view of proximal and intermediate portions of the embodiment of FIG. 1.

FIG. 2A shows a longitudinal sectional view of the intermediate portion of an alternative embodiment.

FIG. 3 shows a longitudinal sectional view of the intermediate and distal portions of the embodiment of FIG. 1.

FIG. 4 shows a longitudinal sectional view of a distal portion of the embodiment of FIG. 1.

FIG. 5 shows a longitudinal sectional view, similar to that of FIG. 4, showing an alternative construction of the distal portion of the embodiment of FIG. 1.

FIG. 5A shows a cross sectional view taken along lines A–A' of FIG. 5.

FIG. 6 is a side view of a first liner that is optionally used with the embodiment of FIG. 1.

FIG. 6A is a cross sectional view along line A—A of FIG. 6.

FIG. 6B is a cross sectional view along line B—B of FIG. 6.

FIG. 6C is a cross sectional view along line C—C of FIG. 6.

FIG. 7A is a longitudinal sectional view of the proximal portion of the embodiment of the first liner of FIG. 6.

FIG. 7B is a longitudinal sectional view of the intermediate portion of the embodiment of the first liner of FIG. 6.

FIG. 7C is a longitudinal sectional view of the distal portion of the embodiment of the first liner of FIG. 6.

FIG. 8 is a side view of a second liner that is optionally used with the first liner of FIG. 6 and the embodiment of the therapy selection sheath of FIG. 1.

FIG. 8A is a cross sectional view along line A—A of the embodiment of the second liner of FIG. 8.

FIG. 8b is a cross sectional view along line B—B of the embodiment of the second liner of FIG. 8.

FIG. 9 shows the first liner of FIG. 6 and the second liner of FIG. 8 assembled together with the embodiment of the sheath of FIG. 1.

FIG. 10 shows a longitudinal sectional view of an intermediate portion of the assembled first and second liners and sheath as in FIG. 9.

FIG. 11 shows a side view similar to FIG. 9 with the assembled first and second liners and the sheath used in conjunction with a guide catheter and a guide wire.

FIG. 12 shows a longitudinal sectional view of an intermediate section of the assembled devices of FIG. 11.

FIG. 13 shows a longitudinal sectional view showing use of the therapy selection sheath of FIG. 1 for positioning of other intravascular devices in a patient's vasculature.

FIG. 14 shows a longitudinal sectional view of the assembled devices of FIG. 13 depicting another stage of the procedure.

FIG. 15 shows a longitudinal sectional view of another embodiment of the present invention.

FIG. 16 shows a longitudinal sectional view of yet another embodiment of the present invention incorporating an inflatable member.

FIG. 17 shows a longitudinal sectional view of intermediate and distal sections of a further embodiment of the present invention incorporating a dilation member.

FIG. 18 shows a longitudinal sectional view, similar to that of FIG. 17, of intermediate and distal sections of a further embodiment of the present invention incorporating a dilation member.

FIG. 22 shows a longitudinal sectional view of a still further embodiment of the present invention incorporating a dilation member.

FIG. 22A is a cross section of the embodiment of FIG. 22 taken along line A–A'.

FIG. 22B is a cross section of the embodiment of FIG. 22 taken along line B–B'.

FIG. 22C is a cross section of the embodiment of FIG. 22 taken along line C–C'.

FIG. 23 shows a longitudinal sectional view showing an intermediate portion of the embodiment of FIG. 22.

FIG. 24A shows a longitudinal sectional view, similar to FIG. 23, showing an intermediate portion of an alternative embodiment.

FIG. 24B shows a longitudinal sectional view, similar to FIGS. 23 and 24A, showing an intermediate portion of an alternative embodiment.

FIG. 27 shows a side view showing a distal portion of an alternative embodiment.

FIG. 28 shows a side view showing a distal portion of a further alternative embodiment.

FIG. 28A shows a cross sectional view along line A—A of FIG. 28.

DETAILED DESCRIPTION OF THE PRESENTLY PREFERRED EMBODIMENTS

I. First Presently Preferred Embodiment

Figure 16A:
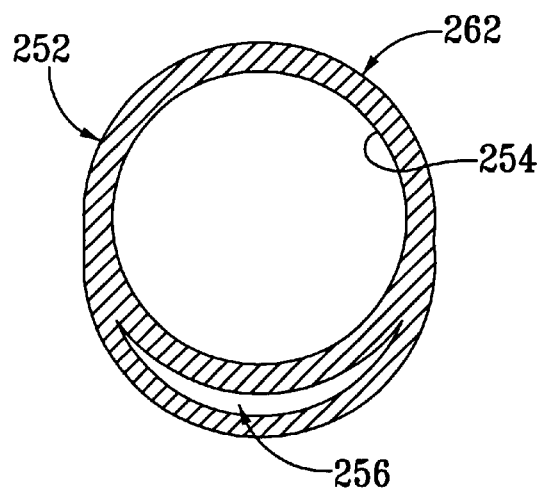
FIG. 16A is a cross section of the embodiment of FIG. 16 taken along line A–A'.

Referring to FIGS. 1–14, there is depicted an embodiment of the present invention. Description of the first preferred embodiment will include a delivery sheath embodiment of the present invention, liners that are optionally used in conjunction with the delivery sheath, and exemplary methods for using the delivery sheath in conjunction with the selective intravascular delivery of multiple intravascular devices.

A. Delivery Sheath

Referring to FIGS. 1–5, there is a selective delivery sheath or introducer 10. The therapy selection sheath 10 has a proximal end 12 and a distal end 14. The therapy selection sheath 10 is used to position multiple other intravascular devices into the vascular system of a patient. These other intravascular devices may be of any type and are selected by the physician based upon an assessment of the most suitable device for the needs of the patient. The therapy selection sheath 10 allows for alternate advancement of one or another of the multiple devices into a distal region of the patient's vascular system.

The therapy selection sheath 10 includes an elongate tubular body 16. The tubular body 16 includes three sections: a proximal section 20, an intermediate section 22, and a distal section 24. The elongate tubular body 16 has a lumen 28 that extends therethrough. More specifically, the lumen 28 includes three portions that correspond to the three sections of the tubular body 16. A portion 28a of the lumen 28 extends through the proximal section 20, a portion 28b of the lumen 28 extends through the intermediate section 22, and a portion 28c of the lumen 28 extends through the distal section 24. The tubular body 16 is dimensioned to receive two other intravascular devices in the intermediate lumen section 28b. The other intravascular devices may include such devices as guide wires, ultrasonic imaging devices (such as the devices described in copending applications Ser. Nos. 07/668,919 filed Mar. 13, 1991 and 07/840,917 filed Feb. 21, 1992 the entire disclosures of which are incorporated herein by reference), fiber optic imaging devices, electrical field imaging devices, other imaging devices, ablation devices such as electrophysiology nodal ablation, recanalization devices (such as the devices described in copending application Ser. No. 07/826,959, filed Jan. 24, 1992, the entire disclosure of which is incorporated herein by reference), flowmeter devices such as Doppler, monitor devices, manometers, stent placement devices, drug delivery devices, balloon catheters (e.g., over-the wire, fixed wire, isolation balloon catheters), other dilating devices (e.g., bougies), laser angioplasty devices, atherectomy devices, angioscopes, endoscopes, other visualizing devices, devices for delivering occluding means (e.g., foams, drugs, and detachable balloons), retrieval devices, destructive devices for disintegrating or lysing obstructions, and so on. A conventional guide wire placed in lumen 28 may additionally receive devices such as those mentioned above, including for example coaxial balloon catheters of low profile, other low-profile dilators, ultrasonic imaging devices, fiber optic and other imaging devices, ablation devices such as electrophysiology nodal ablation, recanalization devices, flowmeter devices such as Doppler, monitor devices, manometers, stent placement devices, drug delivery devices, balloon catheters, other dilating devices (e.g., bougies), laser angioplasty devices, atherectomy devices, angioscopes, endoscopes, devices for delivering occluding means (e.g., foams, drugs, and detachable balloons), retrieval devices, and destructive devices for disintegrating or lysing obstructions.

The lumen 28b is dimensioned so that two such other intravascular devices can occupy a position adjacent to each other, e.g. side-by-side, in the intermediate section 22 of the tubular body 16. The lumen 28c in the distal section 24 of the tubular body is dimensioned such that only a single one of the other intravascular devices can occupy a position in the lumen 28c in the distal section at a time. This allows the multiple intravascular devices to be available and already positioned in the therapy selection sheath 10 and ready to be advanced distally for use in the vascular system of the patient. Also, the therapy selection sheath provides for the multiple devices to be easily alternated, as needed, without being withdrawn entirely from the patient's body. Furthermore, the therapy selection sheath provides a small outer profile in the distal section 24 that allows it to be advanced and positioned in a distal portion of a patient's vascular system.

In order for the therapy selection sheath to provide for the positioning of multiple other intravascular devices, the dimensions of the sections of the therapy selection sheath are chosen taking into account the sizes of the intravascular devices, or classes of intravascular devices, with which it would be used. Accordingly, when it is explained, for example, that the intermediate section 22 is sized to accommodate two other intravascular devices in the lumen 28b and that the distal section 24 is sized to accommodate only one of the two intravascular device in the lumen 28c alternately, it should be understood that these relationships refer to intravascular devices of predetermined sizes. The predetermined sizes of these two other intravascular devices are not necessarily the same. The distal section lumen 28c is sized to accommodate only one (not both) of the intravascular devices at a time, so the distal section lumen 28c is large enough to accommodate the intravascular device of the larger predetermined size (since the smaller device could easily be accommodated as well). However, the distal section lumen 28c is not large enough to accommodate both the intravascular device of the larger size and the intravascular device of the smaller size at the same time. On the other hand, the intermediate section lumen 28b is sized to accommodate both the intravascular device of the larger size and the intravascular device of the smaller size at the same time.

Certain sizes of intravascular devices have become conventional or at least common for use with respect to certain therapeutic procedures. Such sizes are dictated in part by anatomical considerations and in part by engineering and handling considerations. For example, in a present embodiment of the present invention for use in treating a total occlusion in the coronary arteries, the therapy selection sheath 10 is used in conjunction with a sonic recanalization device and a guide wire. In the present embodiment, the sonic recanalization device has a distal outer diameter of approximately 0.035 inches. A conventional intravascular coronary guide wire may be used having a size of 0.018 inches. Accordingly, an embodiment of the therapy selection sheath for use with these intravascular devices would have an intermediate section 22 with a lumen 28b sized to accommodate two adjacent, or side-by-side, intravascular devices —the sonic recanalization device and the guide wire, each having a predetermined size of 0.035 inches and 0.018 inches, respectively. The distal section lumen 28c of the therapy selection sheath has a size that would accommodate advancement of the sonic recanalization device or the guide wire. However, the lumen 28c would not be large enough to accommodate both the recanalization device and the guide wire next to each other at the same time.

Referring again to FIG. 1, at a proximal end 12 of the tubular body 16 is a manifold 40. The manifold 40 has two ports or openings: a main port 42 and an auxiliary port 44. Both the main port 42 and the auxiliary port 44 communicate with the lumen 28 of the tubular body 16. The manifold 40 is preferably made of a hard plastic material such as polycarbonate. In one present embodiment, the manifold 40 is made of a two-piece construction, as shown in FIG. 1, although a single-piece construction would be acceptable as well. The manifold 40 may also be constructed with fewer or more than two ports.

A hemostasis clamp of conventional design is preferably provided in a location outside the patient's body in the proximal section 20. Alternately, an O-ring may be provided in the manifold 40 to function as a hemostasis clamp.

The proximal section 20 of the tubular body 16 is connected to the manifold 40, as shown in FIG. 2. In this embodiment, the lumen 28 in the proximal section 20 has a dimension that permits only a single intravascular device to occupy a position in the lumen 28a therein at a given time. In this embodiment, the lumen 28a in the proximal section 20 has a diameter of 0.040 inches. In this embodiment, the proximal section 20 has a length of approximately 97 cm. The proximal section 20 is made of a relatively stiff material to permit positioning and advancement of the therapy selection sheath. In this embodiment, the proximal section 20 is made of high density polyethylene. A strain relief 48 may be located at the proximal end of the proximal section 20 at the connection of the proximal section to the manifold 40. The strain relief 48 may be approximately 5 cm in length (approximately 0.75 cm of which may extend into the bore of the manifold). The strain relief may be made of low- to medium-durometer urethane.

Occupying a position immediately distal of the proximal section 20 is the intermediate section 22. The lumen 28b in the intermediate section 22 is dimensioned so that two intravascular devices of predetermined sizes can be positioned in the lumen 28b in the intermediate section 22. The lumen 28b in the intermediate section 22 may be circular or may have a shape other than circular as long it possesses a size sufficient to accommodate the two other intravascular devices of the predetermined sizes. In the present embodiment, the lumen 28b of the intermediate section is circular and has a diameter of 0.056 inches. Also, in this embodiment, the intermediate section 22 has a length of approximately 10 cm. The intermediate section 22 may be made of the same material as the proximal section 20. In a preferred embodiment, the proximal and intermediate sections are made of a single piece of high density polyethylene tubing that is necked or otherwise processed to produce the smaller-dimensioned proximal section.

One of the two intravascular devices that will occupy a position in the intermediate section 22 can extend proximally into the lumen 28a in the proximal section 20, through the manifold 40 and proximally out the proximal end of the manifold. This first intravascular device may be loaded into the sheath from either the proximal end or the distal end (i.e. back-loaded). The other of the intravascular devices that will occupy a position in the intermediate section 22 exits the intermediate section 22 proximally via an intermediate section proximal opening 50. The intermediate section proximal opening 50 is located at a proximal end of the intermediate section 22 through a wall of the tubular body 16. The intermediate section proximal opening 50 is oriented in a proximal direction. The second intravascular device can also be loaded into the sheath either proximally from the intermediate section proximal opening 50 or distally from a distal opening, (i.e. backloaded). Thus, after the two intravascular devices are positioned in the sheath, one of the two intravascular devices that occupies a position in the lumen 28b in the intermediate section 22 will extend proximally into the lumen 28a in the proximal section 20, and the other intravascular device that occupies a position in the intermediate section 22 will extend proximally outside of, but along side of, the tubular body 16 along the proximal section 20. The proximal section 20 is preferably offset from the longitudinal axis 52 of the intermediate section 22 to facilitate the side-by-side, or adjacent, accommodation of the intravascular devices into the intermediate section.

Also in a preferred embodiment, the intermediate section includes openings 54. These openings 54 are preferably used for dye injections, as explained below, but may also be used for other therapeutic or diagnostic fluid delivery, (i.e. drug delivery, for example) or perfusion. The openings 54 are spaced along the length of the intermediate section starting approximately 1.5 cm distally of the intermediate section proximal opening 50. Approximately 6 openings are located in the intermediate section 22. These openings 54 are spaced approximately 3 cm apart. Each opening is approximately 0.02 inches in diameter. In a preferred embodiment, the openings 54 are staggered around the circumferential surface of the intermediate section 22. The openings may have other alternative configurations and alternatively may be located in the distal, intermediate, and/or proximal sections.

Occupying a position immediately distal of the intermediate section 22 is the distal section 24. The lumen 28c in the distal section 24 is dimensioned so that only one of the two intravascular devices of the predetermined sizes can be advanced distally from the intermediate section 22 and positioned into and occupy a position in the lumen 28c in the distal section 24. In this embodiment, the distal section 24 has an outer diameter of 0.052 inches and a wall thickness of 0.004 inches. Therefore, the lumen 28c in the distal section 24 has a diameter of 0.044 inches. In this embodiment, the distal section 24 has length of approximately 18 cm. In a preferred embodiment, the distal section 24 is made of a flexible plastic material. In a present embodiment, the distal section may be made of polyethylene.

At a distal end of the distal section 24 is a distal lumen opening 58. The distal lumen opening 58 communicates with the lumen 28c and has a diameter that corresponds in size to that of the lumen 28c, e.g. 0.038 inches. (Alternatively, in some procedures it may not be necessary to pass the selected instrument with a predetermined size through the distal opening 58 of the distal section 24. In these cases, lumen 28c need only be large enough to accommodate the most distal advancement of the selected device.)

Referring to FIG. 3, in a preferred embodiment, the connection between the distal section and the intermediate section is formed by overlapping a proximal end 59 of the distal section 24 over a necked down distal end 60 of the intermediate section 22. An adhesive, such as 2-part urethane, or other means of attachment may be used to connect the intermediate and distal sections.

Referring to FIGS. 3 and 4, one or more radiopaque markers may be located on the tubular body 16. Preferably, three markers 62, 64, and 66 are located along the distal section 24. The marker 62 is located at the proximal end of the distal section 24 at the connection of the intermediate and distal sections. The second radiopaque marker 64 is located approximately 3 cm from the distal end of the distal section 24. As shown in FIG. 4, the third marker 66 is located at the distal end of the distal section 24. A fourth marker 67 may be placed at the proximal opening 50.

The radiopaque markers 62, 64, 66, 67 may be made of a band or coil of a suitable material such as gold, tungsten, platinum, iridium, or alloys thereof. Each marker is approximately 0.13 cm in length and is connected to the section at which it is located by a suitable bonding process, such as an adhesive.

The markers 62, 64, and 66 may be located on an interior side of the distal section 24 of the sheath, as shown in FIG. 4. Alternatively, these markers may be located on an exterior side of the sheath as shown in FIG. 5. If located on the interior side, a rim 68 may be provided at the distal lumen opening 58 to prevent the marker from exiting the lumen 28c. In further alternative embodiments, the markers may be provided by doping the material of the sheath with radiopaque material, such as barium sulfate or $BiO_3$, on the order of 10–60% by weight or more, so that these locations of the sheath may be observed fluoroscopically.

The distal tip 69 may be tapered, chamfered (as illustrated in FIG. 5), or blunt (as shown in FIG. 4).

B. Optional Liners

Referring to FIGS. 6–8, there are depicted first and second liners 100 and 102. These liners are separate from the therapy selection sheath 10 but may optionally be used in conjunction with it, as explained below, to facilitate use and operation of the sheath with other intravascular devices.

Referring to FIGS. 6–7C, the first liner 100 includes an elongate tubular portion 104 and a handpiece 106. The elongate tubular portion 104 is composed of a tube defining a lumen 110. The elongate tubular portion 104 has a length greater than the therapy selection sheath 10 and an outer diameter less than the diameter of the lumen 28 of the therapy selection sheath so that the elongate tubular portion 104 can be located in the lumen 28 of the therapy selection sheath 10. In an embodiment of the first liner 100 for use with the embodiment of the therapy selection sheath 10, described above, the elongate tubular portion 104 of the first liner 100 is comprised of a tube having an outer diameter of 0.038 inches and an inner diameter of 0.032 inches and a length of 132.6 cm.

The elongate tubular portion 104 of the first liner 100 includes a proximal portion 112, an intermediate portion 114, and a distal portion 116. The proximal portion 112 of the elongate tubular portion 104 connects to the handpiece 106. The handpiece 106 may be made of a hard plastic material such as polycarbonate. A handle portion 118 of the handpiece 106 is sized to be grasped manually. The elongate tubular member 104 is connected to the handpiece 106. A stiffening rod 124 is located in the lumen 110 of the elongate tubular portion 104 in the proximal portion 112, as shown in FIGS. 6A and 7A. The stiffening rod 124 can be made of wire of stainless steel having an outer diameter of 0.018 inches.

In the intermediate section 114, a portion of the wall of the tube member forming the elongate tubular portion 104 of the first liner 100 is removed forming a cutaway 126 so that intermediate section 114 of the first liner 100 has a C-shaped cross section, as shown in FIG. 6B.

The distal section 116 of the elongate tubular member 104 has a slit 128 extending through the wall of the tube from which the elongate tubular member 104 is made, as shown in FIG. 6C. The slit 128 is aligned with the cutaway 126 of the intermediate section 114. Located at a distal end 130 of the distal section 116 is a distal opening 132 communicating with the lumen 110.

With the embodiment of the therapy selection sheath described above, the elongate tubular member 104 of the first liner 100 has a length of 132.6 cm. The proximal section 112 has a length of 100.4 cm, the intermediate section 114 has a length of 26.6 cm, and the distal section 116 has a length of 2 cm. The stiffening rod 124 is approximately 104.5 cm in length. The elongate tubular member 104 of the first liner 100 has an outside diameter of 0.038 inches and an inner diameter of 0.031 inches. In a present embodiment, the first liner is composed of high density polyethylene (HDPE).

Referring to FIG. 8, there is depicted the second liner 102. The second liner 102 is intended to be located in the lumen 110 of the elongate tubular member 104 of the first liner 100 in the distal and intermediate sections, 116 and 114, thereof while the first liner 100 is in the sheath 10. The second liner 102 is provided in a length so that a proximal end 134 of the second liner 102 extends out the proximal guide wire opening 50 of the sheath 10 and a distal end 136 extends out the distal ends, 58 and 132, of the sheath 10 and the first liner 100, respectively.

Referring to FIG. 8, the second liner 102 is composed of a tubular member 137 defining a lumen 138. A slit 140 extends through the wall of the tubular member 137 along the entire length of the second liner 102. In an embodiment of the second liner for use with the first liner 100 and sheath 10, the tubular member 137 has a length of 35 cm, an inner diameter of 0.020 inches and an outer diameter of 0.027 inches. Approximately half the wall of the second liner 102 is cut away for approximately 1 cm at the proximal end 134. In a preferred embodiment, the second liner 102 is composed of HDPE.

C. Assembly of the Sheath and Liners

Referring to FIGS. 9 and 10, there are depicted the sheath 10 and the liners 100 and 102 assembled together and ready for use. The first liner 100 is positioned into the sheath 10 via the port 42 of the sheath manifold 40. The first liner 100 is oriented with respect to the sheath 10 so that the cutaway 126 of the liner intermediate section 114 is in alignment with the intermediate section proximal opening 50. The first liner 100 is advanced through the lumen 28 of the sheath so that approximately 2 mm of the first liner 100 extends out the distal opening 58 of the sheath 10. The second liner 102 is backloaded into the lumen 110 of the first liner 100 from the distal end of thereof. The second liner 102 is advanced in a proximal direction through the lumen of the distal and intermediate sections 116 and 114 of the first liner 100. The proximal end of the second liner 102 is made to exit the intermediate section proximal opening 50 from the first liner lumen 110. The cutaway 126 allows the second liner 102 proximal end to readily exit the first liner lumen as well. When fully positioned, the second liner 102 extends distally of the distal end of the first liner 100 by approximately 1 cm and proximally from the sheath intermediate section proximal opening 50 by about 6 cm.

D. Methods of Use of the Therapy Selection Sheath

The embodiment of the sheath 10, described above, has utility for numerous procedures and enables readily combining different intravascular devices and therapies in manners that have not been possible before. Set forth below are several methods of use of the sheath. It can be appreciated that numerous variations on these examples will be apparent to those familiar with this art. Such variations are contemplated to be within the scope of the invention.

EXAMPLE 1

Use With Liners

As mentioned above, the sheath 10 is used to position multiple intravascular devices. One method of use is depicted in FIGS. 11–14. According to this method of use, the sheath 10 is used to position multiple intravascular devices including a guide wire, a vascular recanalization device and a balloon catheter.

Many presently available interventional therapies require that a therapeutic device, such as an angioplasty balloon catheter, be positioned across the diseased region of the person's vasculature. If the vessel is totally or nearly totally occluded, it may be difficult or impossible to cross the occlusion with a conventional guide wire or balloon catheter. Therefore, it has not been possible to treat such vessel occlusions with effective therapies, such as balloon angioplasty. When the physician encounters a totally or nearly totally occluded vessel, he/she may want to use a device specifically adapted to cross a total occlusion. One such device is an intravascular sonic recanalization device, such as one of the devices described in the copending application No. 07/826,959, filed Jan. 24, 1992, the entire disclosure of which is incorporated herein by reference. The sonic recanalization device may be used to form a passageway through a totally or near totally occluded vessel. After the new passageway is formed, the occlusion may be treated with another interventional therapy, such as balloon angioplasty, in order to make the passageway larger.

According to this example, it is assumed that the physician has initially attempted to cross the lesion in the vessel with a conventional guide wire, but has been unsuccessful because the vessel is totally or nearly totally occluded by the lesion. It may be assumed that access to the vascular system has been made in a conventional manner. This typically includes insertion of an introducer (not shown) into the femoral artery of the patient at a location such as the groin. A guide catheter of conventional design may also be used.

A conventional guide wire 150 and a proximal end of a conventional guide catheter 154 are illustrated in FIGS. 11 and 12. The guide wire 150 may be a conventional guide wire and have an outside diameter of approximately 0.018. A proximal portion 156 of the conventional guide wire 150 is shown to extend proximally out the proximal end of the conventional guide catheter 154. With a conventional coronary guide wire typically having an overall length of approximately 185 cm, about 50 cm of the guide wire typically may extend out a proximal of the guide catheter 154 during use. The physician determines to use the sonic recanalization device in an attempt to cross the lesion and to then attempt to perform a conventional balloon angioplasty. Accordingly, the sheath 10 is employed to position multiple other intravascular devices, such as the sonic recanalization device, the guide wire, and a balloon catheter, as described below, to effect a combination of therapies suitable for the specific patient's needs.

The assembled sheath 10 and first and second liners 100 and 102 are backloaded onto the proximal portion 156 of the guide wire 150, as shown in FIG. 11. The proximal portion 156 of the guide wire 150 is received in the lumen 138 of the second liner 102, as shown in FIG. 12. As mentioned above, the second liner 102 is in the lumen 110 of the first liner 100 which in turn is in the lumen 28 of the sheath 10. The assembled sheath 10 and first and second liners 100 and 102 are advanced onto the proximal portion 156 of the guide wire 150 until a most proximal end 157 of the guide wire 150 extends out the proximal end of the second liner 102 which extends out the intermediate section proximal opening 50 of the sheath 10.

Next, the second liner 102 is peeled off of the guide wire 150. This is done by removing the second liner 102 from the guide wire 150 through the slit 140 in the wall of the second liner 102. Next, the entire second liner 102 is withdrawn from the sheath 10 by pulling the second liner out of the intermediate section proximal opening 50. While this is being done, the second liner is peeled from the proximal end of the guide wire 150. The portion of the guide wire 150 extending out the intermediate section proximal opening 50 may be securely grasped so that the position of the distal end of the guide wire in the patient's vessel site may be maintained while the second liner is being withdrawn. This is preferably done while simultaneously advancing the sheath 10 and the first liner 100 distally over the guide wire 150 and into the guide catheter 154. The stiffening rod 124 located in the proximal section 112 of the first liner 100 contributes to the pushability of the first liner during this step. The sheath 10 and first liner 100 are advanced completely into the guide catheter 154 and out the distal end of the guide catheter up to the site of the total occlusion in the vessel. After the distal end of the sheath 10 is fully positioned close to the occluded vessel site, the first liner 100 is extracted from the sheath 10 by withdrawing it proximally out the sheath 10. The intermediate section 114 and the distal section 116 of the first liner 100 can readily pass the portion of the guide wire 150 extending out the sheath intermediate portion proximal opening 50 because of the cutaway 126 located along the intermediate section and the slit 128 along the distal section. The entire first liner 100 is withdrawn from the sheath 10. After the first liner is withdrawn, the sheath is located in the guide catheter 154 with a distal end of the sheath close to the occlusion. The guide wire is located in the intermediate and distal portions of the sheath and extends out the distal opening 58.

Next, a sonic recanalization device 160 is positioned in the therapy selection sheath 10 via the port 42 of the manifold 40. According to this example, the sonic recanalization device 160 has a distal outside diameter of approximately 0.035 inches. The sonic recanalization device 160 is advanced through the proximal section 20 and into the intermediate section 22. The sonic recanalization device 160 and the guide wire 150 occupy positions adjacent to each other in the intermediate section 22 of the therapy selection sheath 10 as shown in FIG. 14. Next, the distal end of the guide wire is withdrawn proximally into the intermediate section 22. This step may be facilitated by fluoroscopic observation of the marker band 62. Then, a distal end 162 of the sonic recanalization device 160 is advanced past a distal end 164 of the guide wire 150 and into the distal section 24 of the therapy selection sheath 10 and then out the distal lumen opening 58 and into the patient's vasculature.

In the patient's vasculature, the sonic recanalization device 160 may be used to recanalize a vessel obstruction. Procedures for recanalization are described in the copending application Ser. No. 07/826,959, referred to above. If the recanalization is successful, the therapy selection sheath 10 is advanced over the distal end of the sonic recanalization device 160 so that the distal end of the sheath 10 is across the recanalized vessel section. Then, the sonic recanalization device 160 is withdrawn proximally (while observing the marker band(s) fluoroscopically) so that the distal end 162 is in the intermediate section 22. Next, the distal end 164 of the guide wire 150 may be advanced past the distal end 162 of the sonic recanalization device 160, into the distal section 24 of the sheath 10, and out of the distal lumen opening 58 into the vessel. The sonic recanalization device 160 and the guide wire 150 again occupy positions as shown in FIG. 14.

Through the use of the recanalization device 160, the guide wire can now be in a position across the previously total occlusion. The therapy selection sheath 10 and the sonic recanalization device 160 may now be withdrawn from the patient's vessel entirely. This is done while leaving the guide wire 150 across the occlusion. Then, another intravascular device, such as a balloon catheter, may be advanced over the guide wire 150 and an angioplasty may be performed on the vessel region that had been recanalized in part by the sonic recanalization device. Alternatively, an atherectomy device may be advanced over the guide wire to "clean up" the recanalized vessel. Finally, all the intravascular devices, including the guide catheter, may be withdrawn.

EXAMPLE 1A

Use With Alternative Positions

The same procedure described above can be performed with the positions of the guide wire and the sonic recanalization device reversed. That is, the guide wire may be advanced into the intermediate section 22 through the manifold 40 and the sonic recanalization device may be advanced into the intermediate section through the proximal opening 50.

EXAMPLE 1B

Use Without Liners

The same procedure described above may be performed with the therapy selection sheath 10 without the use of the first liner 100 or the second liner 102. For example, the sheath 10 can be provided without the first and second liners. The guide wire 150 can be backloaded into the therapy selection sheath 10, as described above, so that the proximal end 157 of the guide wire is slid through the proximal opening 50. The sheath 10 may be bent slightly at the location of the proximal opening 50 to direct the guide wire out the opening. Alternatively, the sheath may be provided with an internal guide or ramp in the lumen 28 adjacent to the proximal opening 50 to direct the backloaded guide wire to exit the proximal opening 50.

EXAMPLE 1C

Front Loaded Use

A similar procedure may be performed with the therapy selection sheath 10 with front loading of the sheath. If it is known in advance that use of multiple intravascular devices is likely and that therefore the sheath will be employed, the guide wire may be inserted into the sheath while both are outside the body. The distal end of the guide wire may be advanced into the proximal opening 50 and advanced distally so that the distal end of the guide wire extends out the distal opening 58 of the sheath before either are positioned in the guide catheter. Then, the assembled sheath and guide wire are positioned together into the guide catheter. The guide wire may extend distally of the sheath during advancement for purposes of positioning. Once the sheath and guide are in place intravascularly, the sheath may be used for multiple exchanges, as described above.

EXAMPLE 1D

Use With Diagnostics

The therapy selection sheath 10 can also be used in combination with imaging devices. For example, a therapeutic device and a diagnostic ultrasound imaging device may be used to obtain ultrasonic images of the patient's vessel walls prior to, during, and after a therapeutic procedure. In this example, the therapy selection sheath 10 is inserted as described above through a guide catheter. FIGS. 13 and 14 illustrate generally how this procedure would be performed. The same arrangement shown in FIGS. 13 and 14 could be used with a diagnostic device substituted for either the sonic recanalization device 160 or the guide wire 150. A therapeutic device and the ultrasound imaging device may be preloaded within the intermediate section 22 of the therapy selection sheath or may be inserted after the therapy selection sheath is in position near the diseased site. First, the ultrasound imaging device is advanced through distal opening 58. After the images are obtained, the imaging device may be withdrawn to the intermediate section 22, and the therapeutic device, which may be an atherectomy device for example, may be extended from the distal end of the sheath to remove the stenosis. The imaging device may then again be advanced to reassess the diseased section after the atherectomy device is withdrawn.

Alternately, two types of imaging devices could be used and exchanged one for the other with a therapeutic device or simply be exchanged with one another. Depending upon the diseased area, it may be preferable to first insert a forward-looking device, then either a side-looking device or a therapeutic device, then reinsert one of the imaging devices.

EXAMPLE 2

Use for Fluid Injections, Such as Dye

In the event dye injections are desired during use of the examples described above, the therapy selection sheath can be used to provide improved visualization. Referring to FIGS. 13 and 14, the therapy selection sheath 10 is advanced to the location desired for the dye visualization. Then, the intravascular devices that occupy positions in the intermediate section 22 may be withdrawn proximal of the most proximal dye opening 54 in order to provide more room for the dye, however, withdrawal may not be necessary depending upon the size of the devices. Next, dye can be injected into the guide catheter 154. In this embodiment of the therapy selection sheath 10, the proximal section 20 of the sheath has a relatively small diameter since the lumen 28a within it sized to be occupied by only one of the intravascular devices. Therefore, this leaves a substantial annular area around the therapy selection sheath inside the guide catheter for dye injection. When the dye gets to the dye openings 54, it will tend to flow into the therapy selection sheath and out through the distal opening 58, thereby delivering dye to the distal end of the sheath.

Although the above described procedure relates to injections of dye for visualization purposes, it is clear that in a similar manner, the therapy selection sheath 10 can be used for delivery of any fluids, such as saline, drugs, or gene therapy with or without a device in place.

EXAMPLE 3

Use for Perfusion

The therapy selection sheath 10 can also be used as a perfusion catheter. When crossing a total or near total occlusion, the vessel is or can become ischemic. It is important when performing a procedure to cross such an occlusion that blood flow be maintained or re-established quickly. In this example, again referring to FIGS. 13 and 14, the recanalization device 160 or guide wire 150 is inserted into the therapy selection sheath 10. The occlusion is crossed, and the therapy selection sheath 10 is advanced through the occlusion to maintain a position and to allow blood flow through the therapy selection sheath 10 to the ischemic area.

II. Further Alternative Embodiments

A. Alternative Embodiment of Sheath

An alternative embodiment of the present invention is shown in FIG. 15. In FIG. 15, a therapy selection sheath 170 includes a tubular body 172 having a lumen 174 extending therethrough and a manifold 176 connected to a proximal end 178 of the tubular body 172. In this embodiment, the tubular body 172 has two sections: a proximal section 180 and a distal section 182. The distal section 182 of this embodiment is similar to the distal section 24 of the embodiment shown in FIGS. 1–14. The portion of the lumen 174 in the distal section 182 is sized to accommodate only a single intravascular device of the predetermined sizes. The portion of the lumen 174 in the proximal section 178 is sized to accommodate two intravascular devices of the predetermined sizes. In this embodiment, the portion of the lumen 174 that can accommodate two intravascular devices of predetermined sizes extends all the way proximally to the manifold 176. The manifold 176 also can accommodate two intravascular devices of the predetermined sizes. The manifold includes a main bore 184 that communicates with the lumen 174. Two ports 186 and 188 branch off from the main bore 184 so that each of the two intravascular devices can be inserted into the therapy selection sheath 170 via separate ports. Use of this embodiment of the therapy selection sheath 170 would be similar to the embodiment 10 shown in FIGS. 1–14.

B. Other Alternative Sheath Embodiments

In alternative embodiments where the therapy selection sheath is used in conjunction with other intravascular devices of sizes that differ from the example above, the dimensions of the lumen in the intermediate and distal sections of the therapy selection sheath would be provided in correspondingly different sizes.

In other alternative embodiments, the therapy selection sheath could be used in conjunction with intravascular procedures in the peripheral arteries. A conventional guide wire for use in the peripheral arteries may have a diameter of 0.035 inches. Accordingly, the dimensions of the therapy selection sheath would be correspondingly different.

In further alternative embodiments, it is contemplated that in some circumstances, the two intravascular devices could be of the same predetermined size. The dimensions of the lumens in each of the sections would be established according to the same functional relationships set out above.

Furthermore, as mentioned above, the lumen 28b in the intermediate section 22 is sized to be large enough to accommodate two intravascular devices of predetermined sizes. It follows therefore, that the intermediate section may be larger than the minimum size necessary to accommodate two intravascular devices of the predetermined sizes. In alternative embodiments, the intermediate section lumen 28b could be provided in a size adequate to accommodate more than two other intravascular devices of the predetermined sizes.

Further embodiments of the therapy selection sheath provide for the proximal section to be of a shape or construction other than tubular, such as solid or flat. In one such embodiment the proximal section could be an elongated member such as a rod. In such an embodiment, the proximal intermediate section opening would be provided in a size sufficient to accommodate the multiple intravascular devices that can occupy positions adjacent to each other in the intermediate section lumen of the sheath.

Yet still another alternative embodiment, more than two openings could be provided in the intermediate section to allow multiple devices to enter the intermediate section.

The therapy selection sheath may be formed of materials other than HDPE, such as other polymers, composites, metals. Several materials having properties known to be desirable for the therapy selection sheath include carbon graphite epoxy and polyamide.

In yet further alternative embodiments, the length of each of the three sections of tubular body 16 would vary with respect to one another depending upon the intended use. For example, one circumstance may require the combined length of the distal and intermediate sections to be shorter than the length of the proximal section. Conversely, other applications may require the distal section be longer than the proximal section. Likewise, the overall length of the therapy selection sheath may also vary depending upon the intended use or vascular approach. The length of the intermediate section could be various lengths greater than zero cm.

Yet further alternative embodiments may include separate passageways or lumens in the proximal and/or intermediate sections for multiple devices while still maintaining a smaller cross-sectional distal profile that would allow only one or possibly more than one device to extend through or into the distal section. These alternative constructions may be similar to those disclosed in application Ser. Nos. 07/704,828 and 07/809,715, referred to above.

The therapy selection sheath may also be constructed such that it can be left in the vasculature for an extended length of time. For example, the therapy selection sheath can be used for placing stents, which are often held in place for anywhere from a few minutes to a few days.

In a still further embodiment, the sheath therapy selection sheath may be formed of an expandable material. According to this embodiment, the proximal, intermediate and/or distal sections of the therapy selection sheath may be made of a material that is expandable to accommodate the devices loaded therein. Referring to FIG. 2A, there is a sectional view of an embodiment in which the intermediate section 22 of the therapy selection sheath is formed of an expandable and/or elastic material such as synthetic rubber or latex. In this embodiment for example, the expandable material has an unstretched lumen size that is less than the diameters of the two other intravascular devices that are intended to be positioned therein. However, because the intermediate section is made of an expandable material, when the two other intravascular devices are advanced into the intermediate section, the walls of the sheath expand (i.e. stretch out) to a size 22' to accommodate the two other intravascular devices. Thus, with this embodiment, the sheath can be used to accommodate a range of sizes of other intravascular devices.

C. Sheath Incorporated With Therapeutic and/or Diagnostic Functions

The above described embodiments disclose a sheath that can be used to delivery multiple other intravascular devices into the vasculature. It is further contemplated that an embodiment of the sheath can be incorporated into an intravascular device that provides either a therapeutic or diagnostic function as well. Because of the unique structure of the therapy selection sheath, the device can be constructed to present a multitude of therapies and diagnostic devices, some of which may require additional lumens or channels for fluid or energy supply. For example, a distal balloon can be provided as a micro-pore or slow-leak balloon or be so constructed and used as a pulsating balloon to dissipate wave form energy through the balloon to disrupt atherosclerotic plaque. Instead of a distal balloon, almost any type of interventional device can be provided with the therapy selection sheath delivery geometry so that any of several devices could be positioned in the distal section. Such devices include, for example, flow monitor devices, Doppler devices, sonic and ultrasonic devices, RF emitters, thermal devices, heat coils, nuclear bands, spark discharge ablation devices, transducer, electrodes, vibrating devices, filters, sensors, and fiber optics. In this example the therapy selection sheath 10 becomes a therapeutic or diagnostic device in addition to providing for the introduction and quick exchange of other intravascular devices. This configuration provides for the use of a minimum of three procedures or devices. For example, two devices could be positioned within the therapy selection sheath while the therapy selection sheath itself could have a third device in association with its intermediate section or distal section, while still allowing for fluid delivery. Such embodiments not only provide the therapeutic or diagnostic capability incorporated already into the device, but additionally possess the capability to provide other therapeutic or diagnostic functions by providing accommodation for multiple other intravascular devices, in a manner similar to the sheath embodiments described above.

1. Sheath With Inflatable Balloon

Figure 16B:
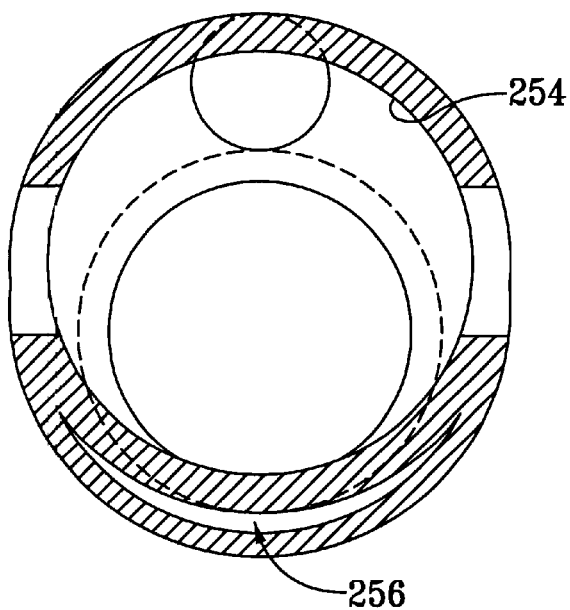
FIG. 16B is a cross section of the embodiment of FIG. 16 taken along line B–B'.
Figure 16C:
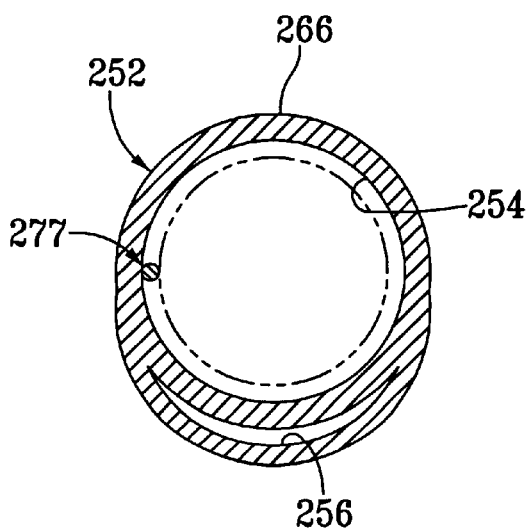
FIG. 16C is a cross section of the embodiment of FIG. 16 taken along line C–C'.

An intravascular balloon catheter according to this embodiment is depicted in FIGS. 16–16C. In FIG. 16, the therapy selection sheath construction is incorporated into a balloon catheter 250. The balloon catheter 250 may be used to perform conventional balloon angioplasty procedures or may be used for other intravascular purposes such as stent delivery, occlusion of vessels, drug delivery, and so on. In this embodiment, the catheter 250 includes a tubular body 252 having a device lumen 254 and an inflation lumen 256 extending therethrough. A manifold 258 is connected to a proximal end 260 of the tubular body 252. As in the embodiment shown in FIGS. 1–4, the tubular body 252 has three sections: a proximal section 262, an intermediate section 264, and a distal section 266. The portion of the device lumen 254 in the distal section 266 is sized to accommodate only a single intravascular device of the predetermined sizes. The portion of the device lumen 254 in the intermediate section 264 is sized to accommodate two intravascular devices of the predetermined sizes. As in the embodiment in FIGS. 1–4, an intermediate section lumen proximal opening 268 is located at a proximal end of the intermediate section 264. The portion of the device lumen 254 in the proximal section 262 is sized to accommodate a single intravascular device of the predetermined sizes. The proximal end of the device lumen 254 communicates with a port 272 of the manifold 258. The manifold also has another port 274 that communicates with the inflation lumen 256. The inflation lumen 256 communicates with the interior of an inflatable dilation balloon 276 located at the distal end of the tubular body 252. A radiopaque marker 277 may be located by the inflatable balloon to permit observation fluoroscopically.

This latter embodiment of the present invention may be used to provide distal vessel access for selective therapies, such as drug or gene therapies, in a similar manner as the embodiments described above. This embodiment also allows for a balloon dilation to be performed with the balloon 276 in conjunction with the other selective therapy or therapies.

2. Sheath With Other Therapeutic and/or Diagnostic Functions

Other embodiments may be provided to allow other devices to be incorporated onto the therapy selection sheath. For example, referring again to FIG. 16, rather than a dilating balloon occupying a site in the distal section, any of the following devices could also be incorporated into the therapy selection sheath: flow monitors, Doppler devices, ultrasound or sonic devices, RF emitters, thermal devices, heat coils, a nuclear band, a spark discharge ablation device, transducers, electrodes, an occluding balloon, a vibrator, a filter, sensors, or fiber optics. In addition, wires for steering or conducting wires for electrical or fiber optic connections may be imbedded in the walls.

Still other embodiments may include using the therapy selection sheath as a means for placing devices intravascularly, for gene therapy, or for other energy deliveries.

3. Alternate Embodiments of Sheath With Inflatable Balloon

Referring to FIGS. 17–21, there are depicted other alternative embodiments of a balloon catheter incorporating the therapy selection sheath geometry in order to provide the capability of delivering multiple other intravascular devices in addition to providing for vessel dilation. In these embodiments, inflation fluid for inflating a balloon is conveyed at least in part through the same lumen used to position the multiple other intravascular devices. With this construction, separate lumens for the inflation fluid and the device(s) may be eliminated and the inflation fluid can be conveyed to the inflatable balloon through the same lumen used for the device(s) (i.e. an "innerless" construction, similar to those referred to in U.S. Pat. Nos. 5,032,113, 5,035,705, and 5,085,636, the disclosures of which are incorporated herein by reference). This has the advantage that the overall device profile may be kept relatively small while providing a relatively large internal capacity lumen for inflation fluid and multiple positioning of other intravascular devices.

In order to provide for both balloon inflation and device delivery through the same lumen, these embodiments provide a means for blocking the openings through the wall of the sheath when it is desired to inflate the balloon and then unblocking the openings when it is desired to pass another intravascular device through an opening. These openings include the distal opening, the opening at the proximal end of the intermediate section, and the dye openings, if provided. These several embodiments differ in how this blocking feature is provided.

Referring to FIG. 17, there is depicted a portion of the intermediate and distal ends of an innerless dilation catheter 350 incorporating the therapy selection sheath construction. In FIG. 17, the dilation catheter 350 is illustrated located inside a guide catheter 352. The dilation catheter 350 has dilation balloon 354 at a distal portion of a shaft 356. The shaft 356 possesses the therapy selection sheath construction with a lumen 358 in an intermediate section 360 sized to accommodate multiple other intravascular devices and in a distal section 362 sized to accommodate only one of the intravascular devices. A guide wire 364 is received into the lumen 358 in the intermediate section 360 via a proximal guide wire opening 366. The guide wire 364 extends through the lumen 358 through the intermediate and distal sections 360 and 362 and out a distal opening 368 located distally of the balloon 354.

According to the embodiment of FIG. 17, a sealing member 370 is located at the proximal guide wire opening 366. The sealing member 370 may be formed of a sleeve that forms a close tolerance fit with the guide wire 364. Thus, when the guide wire is in place in the catheter 350, inflation fluid may be conveyed via a proximal manifold port (not shown, but similar to the manifold ports of FIG. 1) that communicates with the lumen 358 in the proximal section 376. The inflation fluid can therefore be conveyed to the balloon 354 to inflate it without concern that the fluid might leak significantly out the proximal guide wire opening 366. The shaft 356 may be used to perform the delivery and exchange of multiple intravascular devices in same manner as the other embodiments described above.

Referring to FIG. 18, there is depicted an alternative embodiment 378 of the innerless dilation catheter incorporating the therapy selection sheath construction. This embodiment is similar to the embodiment of FIG. 17 except instead of providing a sealing member at the proximal guide wire opening 366, the embodiment of FIG. 18 provides a blocking member 380. The blocking member 380 may be formed of a compliant portion of the shaft 356 or an inflatable balloon or other expandable member located in a portion of the dilation catheter 378 that is normally proximal of the distal end 382 of the guide catheter 352 but distal of any openings through the wall of the dilation catheter 378 along the intermediate or proximal sections, 360 and 376, including the proximal guide wire opening 366 or any dye openings 384. If the blocking member 380 is formed of an inflatable balloon, the size and compliance characteristics of the balloon are chosen so that the balloon will readily tend to inflate and form a fluid tight seal between the dilation catheter 378 and the inside wall of the guide catheter 352. With this embodiment, the dilation balloon 354 may be inflated with fluid conveyed via the catheter lumen 358 in the proximal, intermediate and distal sections. Alternatively, inflation fluid may be provided into the lumen 386 of the guide catheter 352. The fluid will be conveyed through the guide catheter and then into the dilation catheter lumen 358 through the dye openings 384 located along the intermediate section 360. The relative sizes the lumen 358 of the dilation catheter 378 and the annular region between the dilation catheter 378 and the inside of the guide catheter 352 will cause the inflation fluid to tend to pass though the intermediate and distal sections of the dilation catheter 378 rather than around them.

Figure 19:
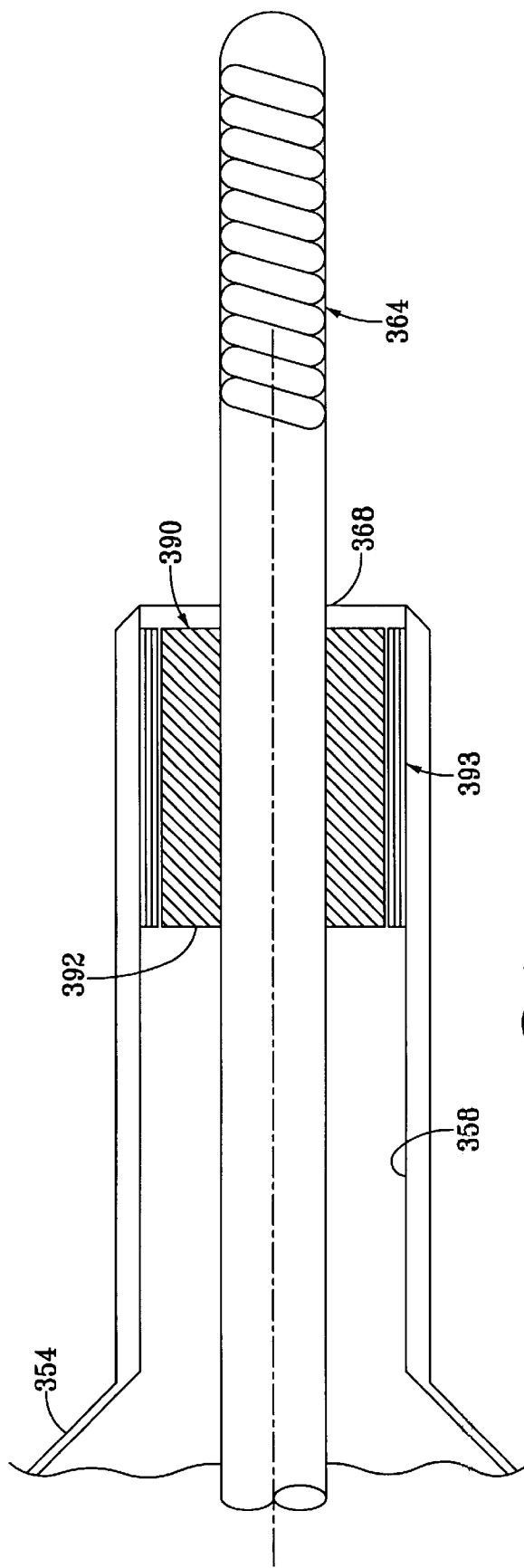
FIG. 19 shows a longitudinal sectional view of a distal section of a further embodiment of the present invention incorporating a dilation member.
Figure 20:
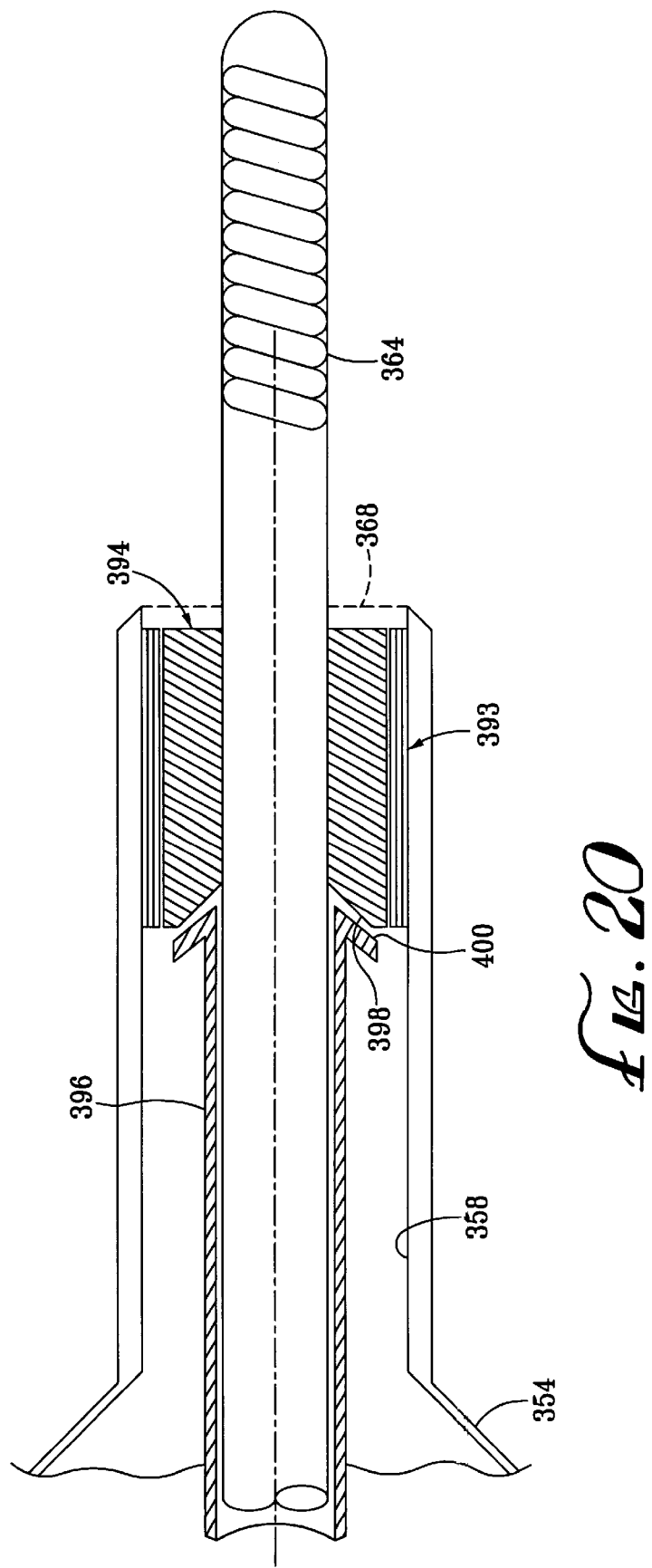
FIG. 20 shows a longitudinal sectional view, similar to FIG. 19, of a distal section of a further embodiment of the present invention incorporating a dilation member.
Figure 21:
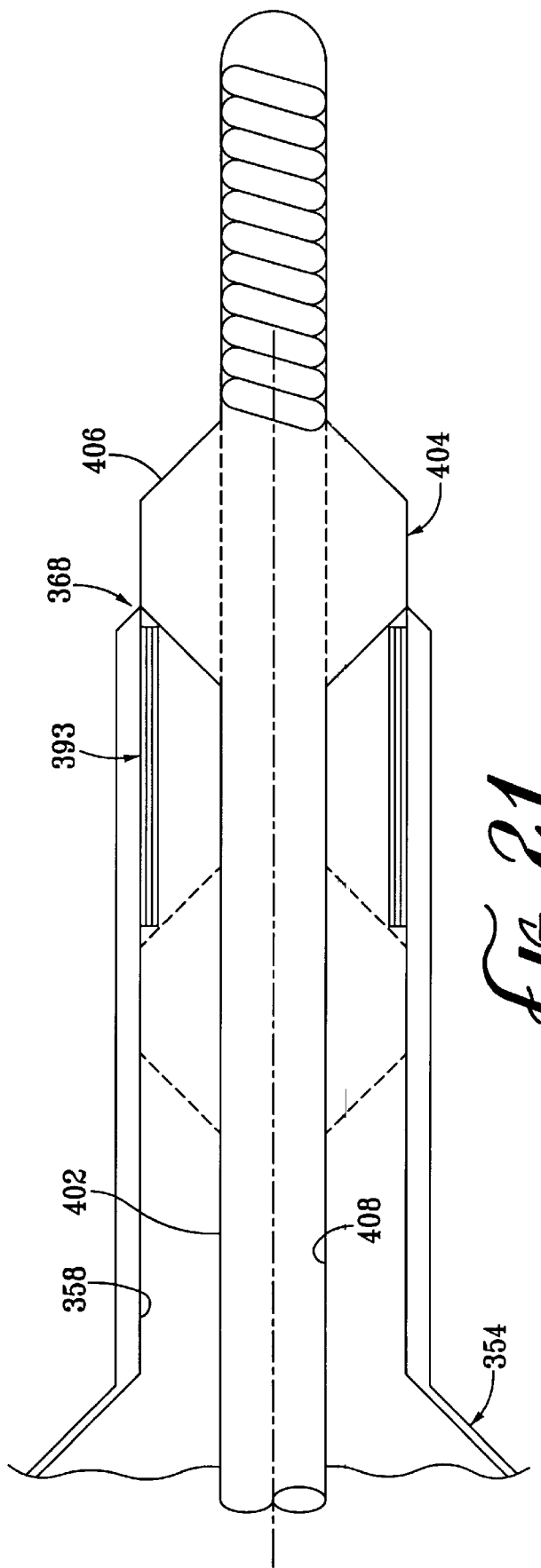
FIG. 21 shows a longitudinal sectional view, similar to FIGS. 19 and 20, of a distal section of a further embodiment of the present invention incorporating a dilation member.

In order to provide an innerless balloon catheter with the therapy selection sheath construction, the distal opening 368 should also be blocked to prevent inflation fluid from leaking out the opening during inflation. FIGS. 19–21 illustrate alternative embodiments of means by which the distal opening 368 can be blocked. Any of the three embodiments of FIGS. 19–21 may be used with the alternative embodiments for blocking the proximal opening 366 illustrated in FIGS. 17 and 18.

Referring first to FIG. 19, a sealing member 390 is incorporated into the lumen 358 in a region distal of the dilation balloon 354. The sealing member 390 comprises a sleeve 392 sized to provide a close tolerance fit around the guide wire 364 extending therethrough. With this embodiment, the guide wire 364 is positioned in the dilation catheter (350 or 378) with the distal end of the guide wire 364 extending through the sleeve 392. The close tolerance fit prevent significant leakage of inflation fluid around the guide wire 364 and out the distal opening 368 when the balloon 354 is inflated. A radiopaque marker 393 may be provided at the distal sealing member 390 to aid in positioning.

Referring to FIG. 20, a sealing member 394 is incorporated into the lumen 358 in a region distal of the dilation balloon 354. This sealing member differs from the sealing sleeve 392, shown in FIG. 19, in that the sealing sleeve of FIG. 20 does not necessarily has a close tolerance fit with the guide wire 364 received therethrough. Instead, this sealing member 394 is used with a separate close fitting guide wire sheath 396. According to this embodiment, the sealing member 394 has a proximal receiving face 398 that has a surface that cooperates with a distal face 400 of the guide wire sheath 396. In a preferred embodiment, the receiving face 398 of the sealing member 394 has a concave surface and the distal face 400 of the guide wire sheath 396 has a tapered conical surface that forms a sealing fit when pressed against the concave surface of the proximal receiving face 398 of the sealing member 394. With the embodiment disclosed in FIG. 20, the guide wire sheath 396 is loaded with the guide wire 364 and permits free movement of the guide wire 364 in the innerless dilation catheter (350 or 378). When inflation of the balloon 354 is desired, the guide wire sheath 396 is pushed distally to form a sealing fit against the sealing member proximal face 398.

Referring to FIG. 21, another alternative embodiment is disclosed for blocking the distal opening 368. According to this embodiment, a guide wire 402 is used that has an expandable portion 404 located near the distal end. The expandable portion 404 may be provided by means of an inflatable balloon 406. The guide wire 402 with expandable portion 404 may include a lumen 408 therethrough for the conveyance of inflation fluid. The dilating catheter (350 or 378) of FIG. 21 would not necessarily be provided with a sealing member at the distal end nor would the catheter of FIG. 21 necessarily form a close tolerance fit around the guide wire 402 at the distal opening 368.

According to this embodiment, when it is desired to inflate the balloon 354, the expandable portion 404 of the guide wire 402 is positioned so that the expandable portion 404 is in the lumen 358 distal of the balloon 354 of the dilation catheter. This may be facilitated by observation of the guide wire 402 with respect to the marker 393 located near the distal opening 368.

Then the expandable portion 404 of the guide wire 402 is inflated to form a seal between the guide wire 402 and the wall of the dilation catheter lumen 358 distal of the balloon 354. The expandable portion 404 of the guide wire 402 may be inside or outside of the lumen 358 provided that the expandable portion 404 forms a sufficient seal. After the lumen 358 is sealed with the expandable portion 404 of the guide wire 402, the balloon 354 of the dilation catheter may be inflated according to the methods described above.

EXAMPLE 4

Alternate Method for Dye Injection Using Occluding Guide Wire

An alternate method for dye injection for visualization incorporates the guide wire 402 with the expanding portion 404, described above. The dye injection method could be performed with the innerless dilation balloon catheter embodiments of FIGS. 17–21 or with any of the previously described embodiments of the therapy selection sheath, described herein, including those that also incorporate a therapeutic or diagnostic function as well as those that do not. According to this method, the guide catheter is positioned proximal of the location desired for the dye visualization or fluid delivery. The guide wire 402 with an expandable portion 404, described above, is inserted into the therapy selection sheath 10 (or dilation catheter with the therapy selection sheath geometry) outside the patient's body so that the guide wire 402 extends through the distal and intermediate sections and exits proximally through opening 50. Alternately, the occluding guide wire can be inserted through the manifold port 40 after the therapy selection sheath 10 is positioned in the patient's body. The therapy selection sheath 10 is then inserted through the guide catheter. The distal opening 58 is occluded with the expandable portion 402 of the guide wire 402 and dye or fluids are injected through lumen 28 and out through openings 54, which can be placed and variously oriented in the distal or intermediate sections.

Alternately, the procedure can be performed without the use of a guide catheter by first inserting a conventional guide wire, then inserting the therapy selection sheath 10 over the guide wire to the site to be visualized or treated, withdrawing the conventional wire to the intermediate section 22 of the therapy selection sheath, inserting the guide wire 402 with an occluding tip to close off the distal opening 58, and then injecting dye or fluids through lumen 28 and out through openings 54.

Alternately, if openings 54 are few and strategically located, opening 50 could be plugged mechanically to allow for fluid flow through openings 54. Likewise, main lumen 28 could be occluded to permit fluid delivery through the annulus between the therapy selection sheath 10 and the guide catheter, through opening 50, and either exiting through openings 54 or distal opening 58.

4. Alternate Embodiments of Sheath With Inflatable Balloon

Referring to FIGS. 22–24A, there is depicted another embodiment of a balloon catheter incorporating the therapy selection sheath geometry in order to provide the capability of delivering multiple other intravascular devices in addition to providing for vessel dilation. This embodiment differs from the embodiment shown in FIGS. 16–16C in that instead of the inflation lumen and the sheath lumen being positioned side-by-side along the proximal, intermediate, and distal sections, another tubular member is located around the therapy selection sheath construction and an inflation lumen is formed by the annular region defined between the sheath and the outer tubular member.

Referring specifically to FIG. 22, the balloon catheter 410 includes a first or inner tubular member 412 that has a geometry and construction similar to any of the embodiments of the therapy selection sheath described above. For example, referring to FIG. 22, the inner tubular member 412 has a proximal portion 414, an intermediate portion 416 and a distal portion 418. A lumen 420 extends through each of these portions and the lumen is sized to accommodate at least two intravascular devices in the intermediate section 416 and one of the intravascular device in a distal section 418. A proximal guide wire opening 422 is located at the proximal end of the intermediate section 416 to permit one of the intravascular devices to extend adjacent the sheath along the proximal section 414. In this embodiment, the inner tubular member 412 is located in a lumen 424 of a second tubular member 426 which is located around the first tubular member 412 defining an annular region 428 between the inner and outer tubular members for conveyance of inflation fluid to a distally located balloon 430 from a proximal inflation port 432 on a manifold 434 connected to a proximal end of the inner and outer tubular members 412 and 426. A radiopaque marker 436 may be located at the balloon 430.

As in the other embodiments of the therapy selection sheath, the intermediate section proximal opening 422 allows for the positioning of another intravascular device into the intermediate section 416 of the inner tubular member 412. It is a feature of this embodiment that a seal 438 is formed around the intermediate section proximal opening 422 where it crosses the annular inflation region 428 to permit access to the intermediate section inner lumen 420 without leakage of inflation fluid around the opening 422. The seal 438 may be formed by an adhesive.

As a further alternative aspect of this embodiment, a directing deflector 440 may be located at the periphery of the intermediate section proximal opening 422. The directing deflector 440 extends laterally from the exterior side wall of the outer tubular member 426 immediately adjacent to the opening 422 to direct another intravascular device into the opening 422. According to one alternative illustrated in FIG. 24A, the directing deflector 440 may be formed of a flexible piece of polymeric material such a portion of the outer wall of the outer tubular member 426. Alternatively as illustrated in FIG. 24B, the directing deflector may have an S-shaped profile.

5. Alternate Embodiment of Sheath With Inflatable Balloon

Figure 25:
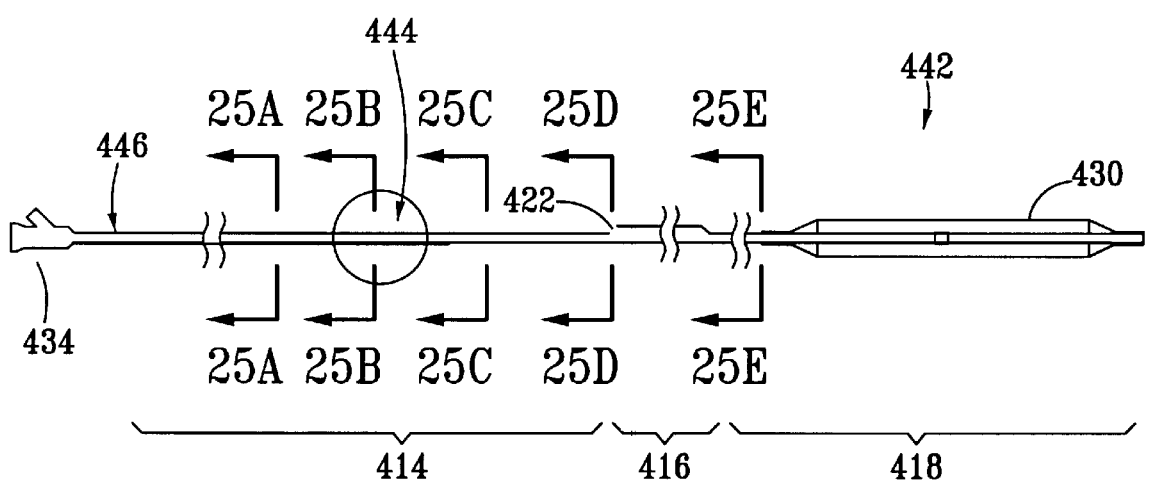
FIG. 25 shows a longitudinal sectional view of a still further embodiment of the present invention incorporating a dilation member.
Figure 25A:
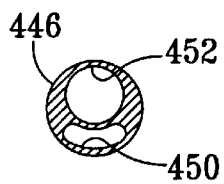
FIG. 25A is a cross section of the embodiment of FIG. 25 taken along line A–A'.
Figure 25B:
FIG. 25B is a cross section of the embodiment of FIG. 25 taken along line B–B'.
Figure 25C:
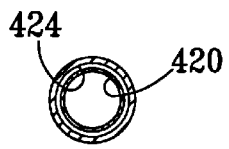
FIG. 25C is a cross section of the embodiment of FIG. 25 taken along line C–C'.
Figure 25E:
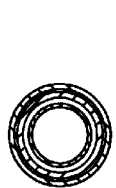
FIG. 25E is a cross section of the embodiment of FIG. 25 taken along line E–E'.
Figure 25D:
FIG. 25D is a cross section of the embodiment of FIG. 25 taken along line D–D'.
Figure 26:
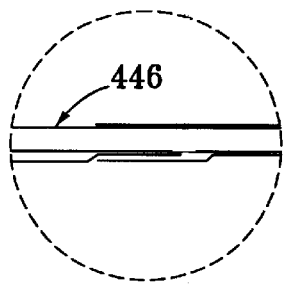
FIG. 26 shows a longitudinal sectional view showing an intermediate portion of the embodiment of FIG. 25.

Referring to FIGS. 25–26, there is depicted another embodiment of a balloon catheter 442 incorporating the therapy selection sheath geometry in order to provide the capability of delivering multiple other intravascular devices in addition to providing for vessel dilation. This embodiment is similar to the embodiment shown in FIGS. 22–24 above, except that instead of the outer tubular member 426 extending all the way proximally to the manifold 434, the outer tubular member 426 extends only part way back along the proximal section 414. At a location 444 along the proximal section 414, a transition is made from a dual lumen extrusion to a coaxial tubular geometry. Referring to FIG. 25, the embodiment of the dilation catheter 442 includes a proximal portion 446. The proximal portion 446 forms part of the proximal section 414 of the dilation catheter 442. The proximal portion 446 is comprised of a tubular member extruded to have a dual lumen extrusion geometry (as illustrated in FIG. 25A). The proximal portion 446 connects to the proximally located manifold 434. The tubular member that forms the proximal portion 446 may be similar to the construction of the proximal section 262 of the dilation catheter 250 shown in FIGS. 16 and 16A. Referring again to FIGS. 24 and 25, in the proximal portion 446, an inflation lumen 450 and the sheath lumen 452 are positioned side by side. At the transition 444, a tubular member bonds over the proximal portion 446. This tubular member may be similar to the outer tubular member 426 of the embodiments of FIGS. 22–24B. The construction of the embodiment of FIGS. 25–26 distally from the transition 444 may be similar or identical to the embodiment depicted in FIGS. 22–24B. At the transition, the inflation lumen 450 is made to communicate with the annular region 428 and the device lumen 452 is made to communicate with the lumen 420.

6. Alternate Embodiment of Sheath With Multiple Balloons

Referring to FIG. 27, there is depicted a distal portion 500 of a further embodiment 502 of a balloon catheter incorporating the therapy selection sheath geometry. This embodiment may possess a construction in its proximal and intermediate sections that is similar to any of the balloon catheter embodiments shown above. The embodiment of FIG. 27 is characterized by the inclusion of multiple balloons along the distal portion of the catheter shaft 503. For example, in the embodiment 502, there is a proximal balloon 506 and a distal balloon 508. These two balloons may be connected in series to a single inflation lumen located in the shaft 503 so that the delivery of fluid inflates both balloons at the same time, or alternatively, the balloons may be provided with separate inflation lumens. In another embodiment, the balloon catheter 502 has an innerless construction, such as shown in any of the embodiments in FIGS. 17–21. In the embodiment shown in FIG. 27, located along the catheter shaft 503 between the balloons 506 and 508 are one or more openings 510. These openings 510 may communicate with a lumen within the shaft, such as either the inflation lumen or the device lumen (or with the single lumen if this embodiment includes an innerless construction as shown in FIGS. 17–21). These openings 510 may be used to deliver drugs or dye into a patient's vessel. According to this embodiment, the balloons 506 and 508 are inflated and then the drugs or dye are delivered through the openings 510 into the region of the vessel occluded between the two balloons. In all other respects, the embodiment of FIG. 27 may be similar to that of the embodiments disclosed above.

7. Alternate Embodiment of Sheath With Perfusion Balloon

Referring to FIGS. 28 and 28A, there is depicted a distal portion 600 of a further embodiment 602 of a balloon catheter incorporating the therapy selection sheath geometry. This embodiment may possess a construction in its proximal and intermediate sections that is similar to any of the balloon catheter embodiments shown above. The embodiment of FIG. 28 is characterized by the inclusion of a perfusion balloon 606 along the distal portion of a catheter shaft 603. In the embodiment 602, the perfusion balloon 606 is formed to have a configuration such that when inflated one or more passages 608 are formed therethrough so that blood can perfusion past the balloon 606. The balloon 606 may be connected to an inflation lumen located in the shaft 603, or alternatively the balloon catheter 602 has an innerless construction, such as shown in any of the embodiments in FIGS. 17–21. According to this embodiment, the balloon 606 may be inflated for extended periods of time since the blood flow through the vessel is not blocked. This embodiment may also be used as a temporary stent, such as during bail-out situations. In all respects, the embodiment of FIG. 28 may be similar to that of the embodiments disclosed above.

It is intended that the foregoing detailed description be regarded as illustrated rather than limiting and that it is understood that the following claims including all equivalents are intended to define the scope of the invention.

We claim:

1. A method for performing an intravascular procedure using a selection sheath said selection sheath having a lumen extending therethrough with an intermediate section and a distal section in which a portion of said lumen in the distal section is dimensioned to be occupied by either one of two intravascular devices of first and second predetermined sizes, but not both at the same time, the method comprising the steps of:

positioning said first intravascular device in said lumen so that a distal end of said first intravascular device extends into said distal section;

positioning said second intravascular device in said lumen so that a distal end of said second intravascular device occupies a position adjacent said first intravascular device in said intermediate section;

advancing said selection sheath into the distal region of a patient's vasculature;

advancing said first intravascular device past said distal section into the distal region of the patient's vasculature;

performing a first procedure with said first intravascular device;

withdrawing said first intravascular device into said intermediate section; and advancing said second intravascular device past said distal section into the distal region of the patient's vasculature.

2. The method of claim 1, further comprising the steps of:

withdrawing said selection sheath and said first intravascular device from the patient's vasculature while maintaining said second intravascular device in the distal region of the patient's vasculature; and advancing a third intravascular device into the distal region of the patient's vasculature over said second intravascular device.

3. A method for performing an intravascular procedure using a selection sheath, said selection sheath having a lumen extending therethrough with an intermediate section and a distal section in which a portion of said lumen in said distal section is dimensioned to be occupied by either one of two intravascular devices of first and second predetermined sizes, but not both at the same time, the method comprising the steps of:

positioning said first intravascular device in said lumen so that a distal end of said first intravascular device extends into said distal section;

positioning said second intravascular device in said lumen so that a distal end of said second intravascular device occupies a position adjacent said first intravascular device in said intermediate section;

withdrawing said first intravascular device proximally to a position at which said distal end of said first intravascular device is proximal of a dye opening located in said intermediate section;

withdrawing said second intravascular device proximally to a position at which said distal end of said second intravascular device is proximal of a dye opening located in said intermediate section; and injecting dye around said selection sheath so that at least some dye flows into said lumen through said dye opening.

4. A balloon catheter comprising:

a shaft having a proximal portion and a distal portion;

said shaft having a first opening along said shaft between said proximal and distal portions, said first opening communicating with a device lumen that extends from said first opening into said distal portion;

an inflatable balloon located at said distal portion of said shaft, said inflatable balloon communicating with an inflation lumen that extends through said distal and proximal portions,;

wherein said device lumen and said inflation lumen are the same lumen along at least a portion of said shaft.

5. The balloon catheter of claim 4 further comprising a sealing member located around said first opening.

6. The balloon catheter of claim 4, wherein at least a portion of said device lumen distally of said first opening is sized to accommodate at least two other intravascular devices of predetermined sizes.

7. The balloon catheter of claim 4, wherein said device lumen is sized to receive a guide wire.

8. The balloon catheter of claim 4, wherein said shaft further comprises a second opening located at a distal end of said shaft and communicating with said device lumen.

9. A balloon catheter comprising:

a shaft having a proximal portion, an intermediate portion, and a distal portion;

said shaft having a first opening along said shaft at said intermediate portion, said first opening communicating with a device lumen that extends from said first opening into said distal portion; and an inflatable balloon located at said distal portion of said shaft, said inflatable balloon communicating with an inflation lumen that extends through said shaft for inflating said balloon;

wherein said device lumen in said intermediate portion of said shaft is sized to accommodate at least a catheter of a first predetermined size and an intravascular device of a second predetermined size;

wherein said device lumen in said distal portion of said shaft is sized to accommodate either said catheter or said intravascular device but not both at the same time;

wherein said device lumen and said inflation lumen are the same lumen along at least a portion of said shaft.

10. A selection sheath, comprising:

an elongate tubular body having a distal section, an intermediate section, and a proximal section;

a distal lumen disposed within said distal section, said distal lumen having a constant cross-sectional area;

an intermediate lumen disposed within said intermediate section and in communication with said distal lumen, said intermediate lumen having a constant cross-sectional area greater than said constant cross-sectional area of said distal lumen; and a proximal lumen disposed within said proximal section and in communication with said intermediate lumen, said proximal lumen having a constant cross-sectional area less than said constant cross-sectional area of said intermediate lumen.

11. The selection sheath of claim 10, wherein said proximal lumen is not in a coaxial relationship with said intermediate lumen.

12. The selection sheath of claim 10, further comprising an intermediate section proximal opening located near a junction of said intermediate section and said proximal section, said intermediate section proximal opening providing access to said intermediate lumen.

13. The selection sheath of claim 12, further comprising:

a removable liner including an elongate tubular portion having a removable liner lumen extending therethrough and a removable liner intermediate section having a cutaway, such that said removable liner intermediate section has a C-shaped cross-section, said removable liner positioned in said proximal lumen and extending into said intermediate lumen, such that said cutaway is aligned with said intermediate section proximal opening; and a splittable liner including an elongate tubular portion having a splittable liner lumen extending therethrough and a slit that extends from splittable liner proximal end to a splittable liner distal end, said splittable liner distal end extending through said removable liner lumen, said splittable liner proximal end extending through said intermediate section proximal opening.

14. The selection sheath of claim 13, further comprising:

a guide wire located in said removable liner lumen; and a sonic recanalization device located in said splittable liner.

15. The selection sheath of claim 10, further comprising a manifold coupled to said proximal section and having a main port in communication with said proximal lumen.

16. The selection sheath of claim 15, wherein said manifold has an auxiliary port in communication with said proximal lumen.

17. The selection sheath of claim 5, further comprising, a plurality of radially positioned apertures on said intermediate section and providing access to said intermediate lumen.

* * * * *